United States Patent [19]

Glasky

[11] Patent Number: 6,027,936
[45] Date of Patent: Feb. 22, 2000

[54] CARBON MONOXIDE DEPENDENT GUANYLY CYCLASE MODIFIERS AND METHODS OF USE

[76] Inventor: Alvin J. Glasky, 12231 Pevero, Tustin, Calif. 92680

[21] Appl. No.: 09/086,878

[22] Filed: May 29, 1998

Related U.S. Application Data

[60] Division of application No. 08/488,976, Jun. 8, 1995, Pat. No. 5,801,184, which is a continuation-in-part of application No. 08/280,719, Jul. 25, 1994, Pat. No. 5,447,936.

[51] Int. Cl.[7] .............................. C12N 5/00; A01N 43/04; A01N 43/42; A01N 43/90; C07D 473/00
[52] U.S. Cl. ......................... 435/325; 514/45; 514/310; 514/262; 544/265; 544/276; 435/7.21
[58] Field of Search .................................. 514/310, 262, 514/45; 544/265, 276; 435/7.21, 325

[56] References Cited

U.S. PATENT DOCUMENTS

| | | | |
|---|---|---|---|
| 3,321,369 | 5/1967 | Glasky et al. | 167/65 |
| 3,438,968 | 4/1969 | Glasky | 260/211.5 |
| 4,035,486 | 7/1977 | Laborit | 424/178 |
| 4,221,910 | 9/1980 | Sorolla | 544/265 |
| 4,952,693 | 8/1990 | Sircan | 544/277 |
| 5,091,432 | 2/1992 | Glasky . | |
| 5,256,677 | 10/1993 | Sham et al. | 514/351 |

OTHER PUBLICATIONS

Sylvain Lehmann et al., "Neurite outgrowth of neurons . . . guanidine group", *Neuroscience Letters*, 1993, 152:57–60, Elsevier Sci. Pub. Ireland Ltd.

Marcia Barinaga, "Carbon Monoxide: Killer to Brain Messenger in One Step", *Science*, Jan. 15, 1993, 259:309.

Ajay Verma et al., "Carbon Monoxide: A Putative Neural Messenger", *Science*, Jan. 15, 1993, 259:381–384.

Min Zhuo et al., "Nitric Oxide and Carbon Monoxide . . . Hippocampus", *Science*, Jun. 25, 1993, 260:1946–1950.

Åke Seiger et al., "Intracranial infusion of purified nerve . . . strategy" *Behavioral Brain Research*, 1993, 57:255–261.

Atsumi Nitta et al., "Effects of oral administration . . . in basal fore–brain–lesioned rats", *Eur. Journal of Pharmacology*, 1993, 250:23–30.

M.H. Tuszynski & F.H. Gage, "Neurotrophic Factors and Neuronal Loss", Ch.25, *Alzheimer Disease*, R.D. Terry et al.,eds., 1994, 405–417, Raven Press, NY.

R.D. Hawkins et al., "Nitric Oxide and Carbon Monoxide . . . Long–Term Potentiation," *Journal of Neurobiology*, 1994, 25:6, pp. 652–665.

S.H. Synder, "NO and CO: The Body's Unprecedented Signaling Molecules," 1995 *Yearbook of Sci. & the Future, Encyc.Brit.*, pp. 96–99.

Copy of the abstract from an article by E. G. Jung (Therampiewoch, vol. 34, No. 17, pp. 2615–2618, 1984) entitled "Chemotherapie Multipler Warzen Mit Inosiplex".

*Primary Examiner*—Hankyel Park
*Attorney, Agent, or Firm*—Oppenheimer, Wolff & Donnelly LLP

[57] ABSTRACT

Disclosed herein are methods directed generally to the control of neural activity and for selectively and controllably inducing the in vivo genetic expression of one or more naturally occurring genetically encoded molecules in mammals. More particularly, the present invention selectively activates or derepresses genes encoding for specific naturally occurring molecules such as neurotrophic factors through the administration of carbon monoxide dependent guanylyl cyclase modulating purine derivatives. The methods of the present invention may be used to affect a variety of cellular and neurological activities and to therapeutically or prophylactically treat a wide variety of neurodegenerative, neurological, and cellular disorders.

16 Claims, 21 Drawing Sheets

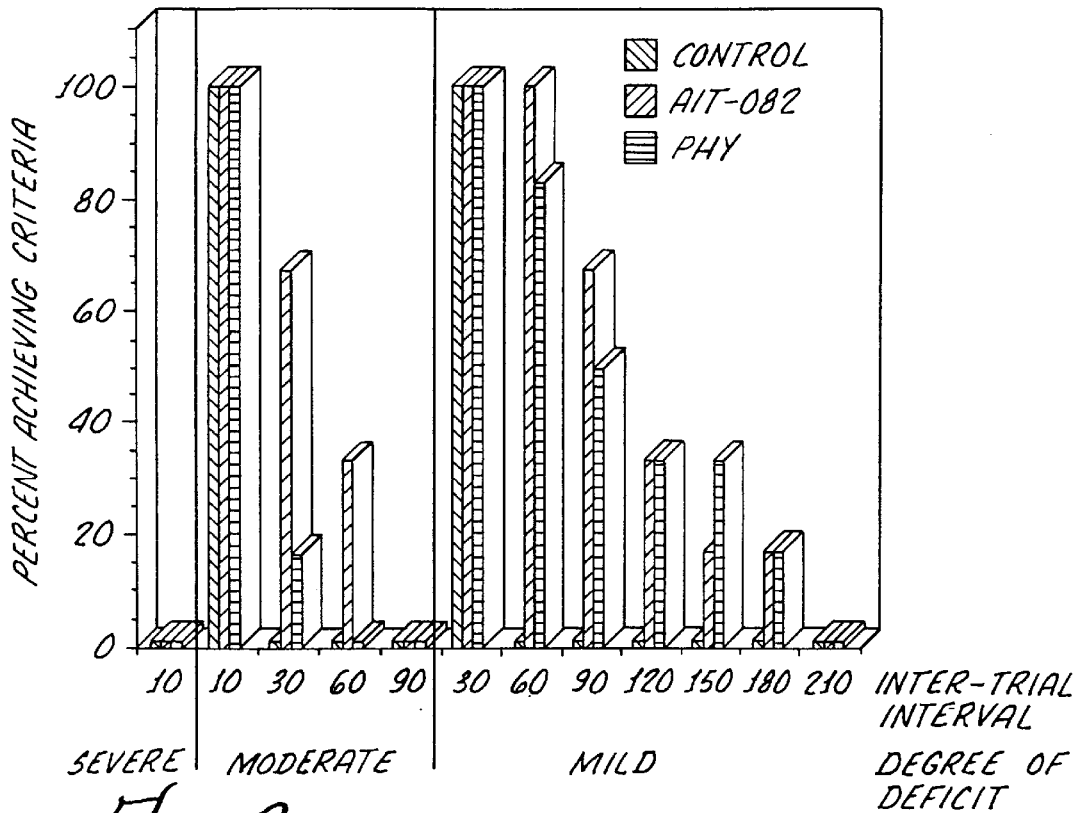
_Fig. 9._
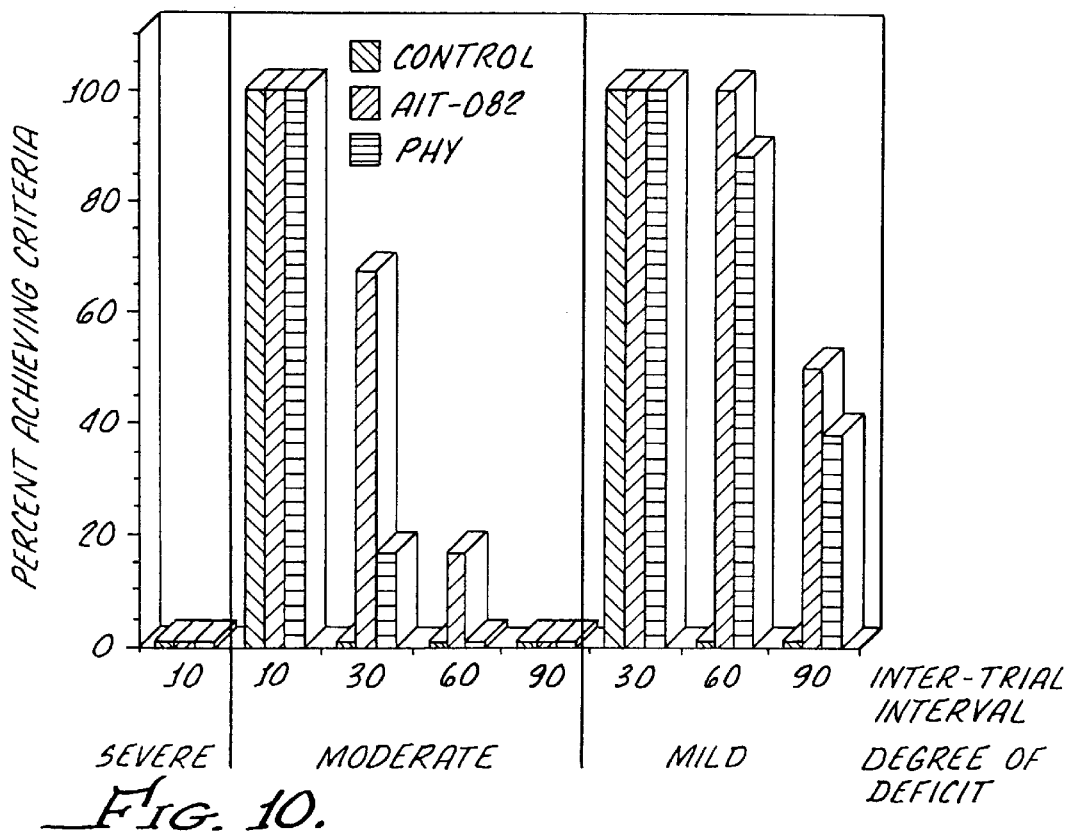
_Fig. 10._

CARBON MONOXIDE DEPENDENT GUANYLY CYCLASE MODIFIERS AND METHODS OF USE

RELATED APPLICATIONS

The present invention is a division of application Ser. No. 08/488,976, filed Jun. 8, 1995, now U.S. Pat. No. 5,801,184, which was a continuation-in-part of application Ser. No. 08/280,719, filed Jul. 25, 1994, now U.S. Pat. No. 5,447, 936.

FIELD OF THE INVENTION

The present invention relates in general to the control of neural activity and to the treatment of neural disorders. More particularly, the present invention is directed to methods for the modification of mammalian neural activity through the administration of carbon monoxide dependent guanylyl cyclase modulating purine derivatives which selectively and controllably induce the in vivo genetic expression of naturally occurring genetically encoded molecules including neurotrophic factors. The methods of the present invention may be used to affect a variety of neurological activities and to therapeutically or prophylactically treat a wide variety of neurodegenerative and neurological disorders.

BACKGROUND OF THE INVENTION

The evolution of the central nervous system in mammals was a natural response to an increasingly complex environment requiring solutions to difficult problems. The resulting structure is an intricate biochemical matrix that is precisely controlled and attenuated through an elaborate system of chemically modulated regulatory pathways. Through an elaborate series of highly specific chemical reactions, these pathways oversee and direct every structural and operational aspect of the central nervous system and, through it, the organism itself Normally the complex interplay of the various control systems cooperates to produce a highly efficient, versatile central nervous system managed by the brain. Unfortunately, when the biochemical matrix of the central nervous system is damaged, either through age, disease or other reasons, the normal regulatory pathways may be incapable of effectively compensating for the loss. In such cases it would be highly desirable to modify or supplement the neural mechanisms to prevent or compensate for such disorders. That is the focus of the present invention.

More specifically, the mammalian brain is composed of approximately ten billion nerve cells or "neurons" surrounded by a even greater number of support cells known as neuroglia or astrocyte cells. Neurons, like other cells of the body, are composed of a nucleus, a cytoplasm and a surrounding cell membrane. However, unlike other cells, neurons also possess unique, fiberlike extensions allowing each individual nerve cell to be networked with literally thousands of other nerve cells to establish a neural infrastructure or network. Communication within this intricate network provides the basis for all mental processes undertaken by an organism.

In each nerve cell, incoming signals are received by neural extensions known as "dendrites" which may number several thousand per nerve cell. Similarly, neural information is projected along nerve cell "axons" which may branch into as many as 10,000 different nerve endings. Together, these nerve cell axons and dendrites are generally termed "neurites" through which each individual neuron can form a multitude of connections with other neurons. As a result, the number of possible neural connections in a healthy brain is in the trillions, giving rise to tremendous mental capacity. Conversely, when the connections within the neural network break down as nerve cells die or degenerate due to age, disease or direct physical insult, the mental capacity of the organism can be severely compromised.

The connection of the individual axons with the dendrites or cell bodies of other neurons takes place at junctions or sites known as "synapses." It is at the synapse that the individual neurons communicate with each other through the flow of chemical messengers across the synaptic junction. The majority of these chemical messengers, or "neurotransmitters," are small peptides, catecholamines or amino acids. When the appropriate stimulus is received by a neural axon connection, the neurotransmitters diff-use across the synapse to the adjacent neuron, thereby conveying the stimulus to the next neuron along the neural network. Based upon the complexity of the information transferred between the nerve cells, it is currently believed that between 50 and 100 distinct neurotransmitters are used to transmit signals in the mammalian brain.

Quite recently, it was discovered that nitric oxide (NO) and carbon monoxide (CO) may function as neurotransmitters. These gaseous molecules appear to participate in a number of neuronal regulatory pathways affecting cell growth and interactions. In the brain, as well as in other parts of the body, CO is produced by the enzyme "heme oxygenase II" (HO). Whether produced from the HO enzyme or from other sources, it is believed that when CO diffuses into a neuron it induces a rise in a secondary transmitter molecule known as "cyclic guanosine monophosphate" (cGMP), by modulating an enzyme known as "guanylate cyclase" or "guanylyl" cyclase. Thus, CO acts as a signaling molecule in the guanylyl cyclase regulatory pathway. The resultant increase in cGMP levels appears to modify several neurotropic factors as well as other neuronal factors which may induce, promote or modify a variety of cellular functions including cell growth and intercellular communication.

Neurotrophic factors are molecules that exert a variety of actions stimulating both the development and differentiation of neurons and the maintenance of cellular integrity and are required for the survival and development of neurons throughout the organism's life cycle. Generally, neurotrophic factors may be divided into two broad classes: neurotrophins and pleiotrophins. Pleiotrophins differ from the neurotrophins in that they lack a molecular signal sequence characteristic of molecules that are secreted from cells and they also affect many types of cells including neurons. Two effects of neurotrophic factors are particularly important: (i) the prevention of neuronal death and (ii) the stimulation of the outgrowth of neurites (either nascent axons or dendrites). In addition, it appears that CO-induced neurotrophic factors may reduce the membrane potential of nerve cells making it easier for the neurons to receive and transmit signals.

Many of today's researchers believe that memory is associated with the modification of synaptic activity, wherein the synaptic connections between particular groups of brain neurons become strengthened or facilitated after repeated activation. As a result, these modified connections activate much easier. This type of facilitation is believed to occur throughout the brain but may be particularly prominent in the hippocampus, a brain region which is crucial for memory. The stimulation of neuronal pathways within the hippocampus can produce enhanced synaptic transmission through these pathways for many days following the original stimulation. This process is known as long term potentiation (LTP).

More particularly, long term potentiation is a form of activity-dependent synaptic electrical activity that is exhibited by many neuronal pathways. In this state, generally accepted as a type of cellular memory, nerve cells are more responsive to stimulation. Accordingly, it is widely believed that LTP provides an excellent model for understanding the cellular and molecular basis of synaptic plasticity of the type that underlies learning and memory in vertebrates, including man.

NO and CO are currently the leading candidates for messenger substances that facilitate LTP because inhibitors of these compounds retard the induction of potentiation. The ability to modify neural activity and to increase the ease of LTP using these or other signal transducers could potentially increase learning rates and cognitive powers, possibly compensating for decreased mental acuity. Prior to the present invention, there were no known agents which could operate on the cellular level int vivo to reliably modify neural regulatory pathways so as to facilitate the LTP of neurons.

In contrast to the enhanced mental capacity provided by long term potentiation, mental functions may be impeded to varying degrees when the neuronal network is disrupted through the death or dysfunction of constituent nerve cells. While the decline in mental abilities is directly related to the disruption of the neural network, it is important to remember that the disruption is occurring on an individual cellular level. At this level the deleterious effects associated with neuronal disruption may be brought about by any one of a number of factors including neurodegenerative diseases and disorders, aging, trauma, and exposure to harmful chemical or environmental agents.

Among the known neurological diseases which adversely impact neuronal function are Alzheimer's disease and related disorders, Parkinson's disease, motor neuropathic diseases such as Amyotrophic Lateral Sclerosis, cerebral palsy, multiple sclerosis, and Huntington's disease. Similar problems may be brought about by loss of neuronal connectivity due to normal aging or through damage to neurons from stroke or other circulatory complications. Direct physical trauma or environmental factors including chemical agents, heavy metals and the like may also provoke neuronal dysfunction.

Whatever the cause of the neural disorder or dysfunction, the general inability of damaged nerve cells to undergo substantial regrowth or regeneration under natural conditions has led to the proposal that neurotrophic factors be administered to nerve cells in order to help restore neuronal function by stimulating nerve growth and function. Similarly, stimulating neuritogenesis, or the growth of neurites, by administering neurotrophic factors may contribute to the ability of surviving neurons to form collateral connections and thereby restore neural function.

At present, prior art techniques and compounds have not been effective or practical to directly administer neurotrophic factors to a patient suffering from a neural disorder. In part, this is due to the complex molecular interaction of the neurotrophic factors themselves and to the synergistic regulation of neural cell growth and neuritogenesis. Neurotrophic factors are the result of a long chemical cascade which is exquisitely regulated on the molecular level by an intricate series of transmitters and receptors. Accordingly, neuronal cells are influenced by a concert of different neurotrophic factors, each contributing to different aspects of neuronal development at different times. Neurotrophic factors are, effectively, the tail end of this cascade and thus are one of the most complex components of the regulatory pathway. As such, it was naive for prior art practitioners to assume that the unattenuated administration of single neurotrophic factors at random times (from the cells viewpoint) could substantially improve cell activity or regeneration. In contrast, modification of the regulatory pathway earlier in the cascade could allow the proper growth factors to be produced in the correct relative amounts and introduced into the complex cellular environment at the appropriate time.

Other practical considerations also preclude the prior art use of neurotrophic factors to stimulate the regeneration of the neuronal network. Neurotrophic factors (including neurotrophins and pleiotrophins) are large proteins and, as such, are not amenable to normal routes of medical administration. For example, these proteins cannot be delivered to a patient or subject orally as the patient's digestive system would digest them before they reached the target neural site. Moreover, due to their relatively large size, the proteins cannot cross the blood brain barrier and access the most important neurological site in the body. Alternatively, the direct injection of neurotrophic factors into the brain or cerebrospinal fluid crudely overcomes this difficulty but is fraught with technical problems of its own which have thus far proven intractable. For example, direct infusion of known neurotrophins into the brain has proven impractical as it requires administration over a period of years to provide therapeutic concentrations. Further, direct injection into the brain has been associated with dangerous swelling and inflammation of the nerve tissue after a very short period of time. Thus, as theoretically desirable as the direct administration of neurotrophic factors to a patient may be, at the present time, it is unfeasible.

Accordingly, it is a general object of the present invention to provide methods and associated compositions for effectively modifying mammalian neurons or neural activity to achieve a variety of beneficial results.

Thus, it is another object of the present invention to provide methods and associated compositions for treating mammalian neurological diseases and disorders.

It is yet another object of the present invention to provide methods and associated compositions for inducing long term changes in the membrane potential of a mammalian neuron.

It is still yet another object of the present invention to provide methods and associated compositions for inducing the iii vivo physiological production of genetically encoded molecules and neurotrophic factors within cells.

It is a further object of the present invention to provide methods and associated compositions for enhancing the neurotogenic effects of neurotrophic factors in a physiological environment.

SUMMARY OF THE INVENTION

These and other objects are accomplished by the methods and associated compositions of the present invention which, in a broad aspect, provide for the selective inducement of the in vivo genetic expression and resultant production of naturally occurring genetically encoded molecules including neurotrophic factors, and for the modification of cellular and neural activity through the treatment of mammalian cells and neurons with at least one carbon monoxide dependent, guanylyl cyclase modulating, purine derivative. As will be appreciated by those skilled in the art, the in vivo activation or derepression of genetic expression and the exemplary modification of neural activity brought about by the methods of the present invention may be expressed in a variety of forms or combinations thereof. For example, the treatment of a mammalian cell or neuron through the teachings of the present invention may result in the cell's direct administration of the in vivo expressed molecule through the enhanced cellular production of various naturally occurring genetically encoded neurotrophic factors or in the stimulation of the activity of those factors and their subsequent effect on naturally occurring neuronal development and survival. The methods of the present invention may also stimulate the growth, development and survival of the cell or neuron directly without the deleterious effects of prior art neurotrophic factor methodology. Further, the present invention may be used to lower or change the membrane potential of the cell, increasing its plasticity and inducing long term potentiation.

Exemplary carbon monoxide dependent guanylyl cyclase modulating purine derivatives useful for practicing the present invention include guanosine, inosine pranobex and 4-(3-(1,6-dihydro-6-oxo-9-purin-9-yl)-1-oxopropyl)amino) benzoic acid (AIT-082) and, unlike prior art compounds, these compounds may be administered directly to a patient either orally or through injection or other conventional routes. These exemplary compounds are nontoxic and will cross the blood-brain barrier as well.

In a further, more specific aspect, the methods and compositions of the present invention may be used for the treatment or prophylactic prevention of neurological diseases and disorders, including those brought about by disease, age, trauma or exposure to harmful chemical agents. By promoting the survival, growth and development of individual neurons and associated cells, the methods of the present invention thereby facilitate the regeneration and development of the neural network and alleviate the manifestations of neural dysfunction. Of course, those skilled in the art will appreciate that pharmaceutical compositions may be formulated incorporating effective concentrations of the carbon monoxide dependent guanylyl cyclase modifying purine derivatives along with pharmaceutically acceptable excipients and carriers. These pharmaceutical compositions may be administered orally, topically or by injection. Moreover, as the active agents used in the methods of the present invention can cross the blood-brain barrier, they do not have to be injected or infused directly into the brain or central nervous system.

In yet another aspect, the methods and compositions of the present invention may be used to induce long term changes in the membrane potential of a mammalian neuron. These long term potentiation changes may lead to increased membrane plasticity with a corresponding enhancement of cellular memory. In turn, this enhanced cellular memory may elevate the mental capacity of the subject leading to faster learning and increased retention of material.

Other objects, features and advantages of the present invention will be apparent to those skilled in the art from a consideration of the following detailed description of preferred exemplary embodiments thereof taken in conjunction with the data expressed in the associated figures which will first be described briefly.

BRIEF DESCRIPTION OF THE DRAWINGS

FIG. 4A shows the neurotogenic response of cells grown in the presence of methemoglobin, a carbon monoxide scavenger; FIG. 4B shows the same response of cells grown in the presence of methylene blue, a guanylyl cyclase inhibitor FIG. 4C shows the response of cells grown in the presence of zinc protoporphyrin IX, a carbon monoxide scavenger;

FIG. 9 is a graphical comparison of learning abilities of age-induced memory deficit Swiss Webster mice treated with the purine derivative AIT-082 and the drug physostigmine;

FIG. 10 is a graphical comparison of learning abilities of age-induced memory deficit C57BL/6 mice treated with the purine derivative AIT-082 and the drug physostigmine;

FIG. 12A illustrates measured nerve growth factor concentrations for neurons grown in the presence of different concentrations of guanosine triphosphate and FIG. 12B illustrates nerve growth factor concentrations for cells grown in the presence of various concentrations of guanosine;

FIG. 13A illustrates nRNA levels of nerve growth factor (NGF) and FIG. 13B illustrates mRNA levels of fibroblast growth factor (FGF);

FIG. 14A illustrates neurotogenic response to various purine derivatives at different concentrations in the presence of nerve growth factor, FIG. 14B illustrates neurotogenic response in the absence of nerve growth factor and FIG. 14C illustrates neurotogenic response to individual purine d erivatives and comb inations of purine derivatives in the presence and absence of nerve growth factor;

FIG. 15A illustrates neurotogenic response to various concentrations of inosine; FIG. 15B illustrates the same neurotogenic response to various concentrations of hypoxanthine and FIG. 15C illustrates the neurotogenic response of neuronal cells exposed to different concentrations of xanthine;

FIG. 20A illustrates the neurotogenic response of cells grown in the presence of methylene blue, a guanylyl cyclase inhibitor, FIG. 20B illustrates the neurotogenic response of cells grown in the presence of various concentrations of LY83583, also an inhibitor of guanylyl cyclase, FIG. 20C illustrates the neurotogenic response of cells grown in the presence of various concentrations of atrial natriuretic factor, a hormone which interacts with guanylyl cyclase;

FIG. 22A shows the neurotogenic response of cells grown in the presence of various combinations of nitric oxide donors and hemoglobin and FIG. 22B shows the neurotogenic response of cells grown in the presence of various combinations of nitric oxide donors and methemoglobin;

DETAILED DESCRIPTION

Figure 1:
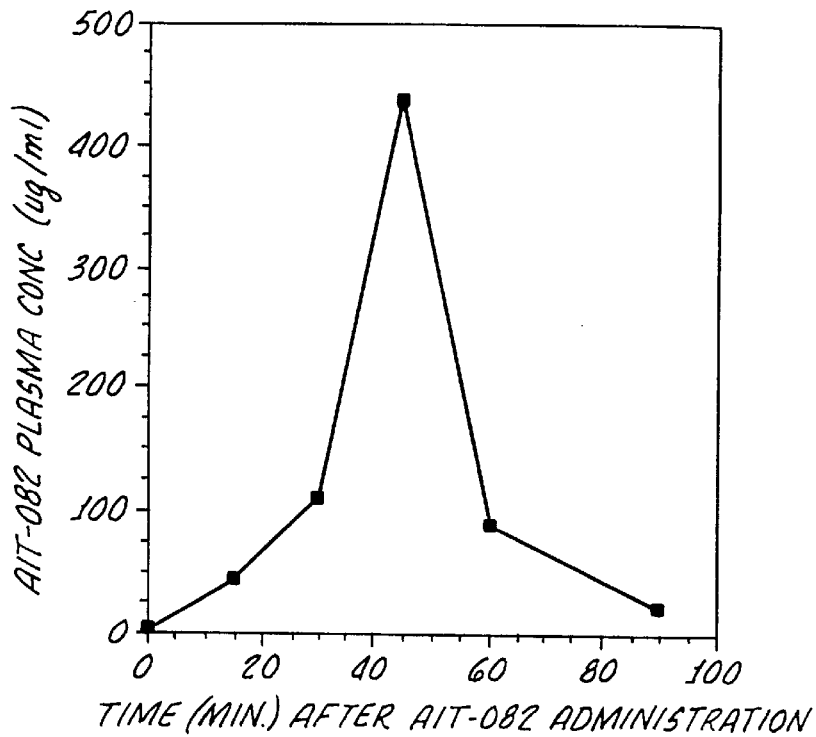
FIG. 1 is a graphical representation of murine plasma concentration following administration of the purine derivative AIT-082 in accordance with the methods of the present invention.

In a broad aspect, the present invention is directed to methods and associated compositions for use in uniquely treating mammalian cells and neurons to modify cellular or neural activity. More specifically, the present invention is directed to the use of effective purine derivatives to modulate the carbon dioxide dependent guanylyl cyclase regulatory system within cells or neurons to produce a variety of beneficial results, including the inducement of in vivo genetic expression of naturally occurring neurotrophic factors and the resultant direct administration of such naturally occurring genetically encoded molecules to a mammal. In exemplary embodiments illustrative of the teachings of the present invention, particular purine derivatives were used to induce genetic expression of encoded molecules, to stimulate neuritogenesis, to enhance neuronal growth and to modify the membrane potential of neurons to produce increased learning capabilities in mammals. Exemplary studies and treatments were performed as discussed below using various dosages and routes of administration of selected exemplary purine derivatives representative of compositions that are effective with the methods of the present invention. Of course, those skilled in the art will recognize that the present invention is not specifically limited to the particular compositions, dosages or routes of administration detailed below.

Depending upon the particular needs of the individual subject involved, the compositions used in the present invention may be administered in various doses to provide effective treatment concentrations based upon the teachings of the present invention. What constitutes an effective amount of the selected composition will vary based upon such factors including the activity of the selected purine derivative, the physiological characteristics of the subject, the extent and nature of the subject's neurodegradation or disorder and the method of administration. Exemplary treatment concentrations which have proven effective in modifying neural activity range from less than 1 $\mu$M to concentrations of 500 mM or more. Generally, initial doses will be modified to determine the optimum dosage for treatment of the particular mammalian subject. The compositions may be administered using a number of different routes including orally, topically, transdermally, intraperitoneal injection or intravenous injection directly into the bloodstream. Of course, effective amounts of the purine derivatives may also be administered through injection into the cerebrospinal fluid or infusion directly into the brain, if desired.

The methods of the present invention may be effected using purine derivatives administered to a mammalian subject either alone or in combination as a pharmaceutical formulation. Further, the purine derivatives may be combined with pharmaceutically acceptable excipients and carrier materials such as inert solid diluents, aqueous solutions or non-toxic organic solvents. If desired, these pharmaceutical formulations may also contain preservatives and stabilizing agents and the like.

The methods of the present invention provide for the long term modification of various types of cellular or neural activity including the in vivo production of naturally occurring genetically encoded molecules such as neurotrophic growth factors (including neurotrophins, pleiotrophins and cytokines), directly administering such in vivo produced molecules, enhancing the effects of these neurotrophic factors, and the stimulation of cell growth and development. Further, the methods of the present invention may be used to promote neuritogenesis, to form collateral nerve circuits, to enhance the production of cyclic purine nucleotides, to enhance synapse formation and to alter the membrane potential of the neuron. These effects may be extremely beneficial in treating neurodegeneration and increasing learning capacity.

For obvious practical and moral reasons, initial work in humans to determine the efficacy of experimental compositions and methods with regard to such afflictions is unfeasible. Accordingly, in the early development of any drug or therapy it is standard procedure to employ appropriate animal models for reasons of safety and expense. The success of implementing laboratory animal models is predicated on the understanding that the cellular or neurophysiology of mammals is similar. Thus, a cellular or neurotropic response in a member of one species, for example, a rodent, frequently corresponds to the same reaction in a member of a different species, such as a human. Only after the appropriate animal models are sufficiently developed will clinical trials in humans be carried out to further demonstrate the safety and efficacy of a therapeutic agent in man.

With regard to neurodegenerative diseases and disorders and to their clinical effects, the mouse model closely resembles the human pathology of these conditions in many respects. Accordingly, it is well understood by those skilled in the art that it is appropriate to extrapolate the mouse or "murine" model to humans and to other mammals. As with humans, mice are susceptible to learning disorders resulting from neuronal degradation, whether due to traumatic injury, age, disease or harmful chemical agents. Just as significantly, neurotropic factors appear to act in substantially the same manner in a murine model as they do in humans with remarkably similar neuronal reactions. Accordingly, for purposes of explanation only and not for purposes of limitation, the present invention will be primarily demonstrated in the exemplary context of mice as the mammalian subject. Those skilled in the art will appreciate that the present invention may be practiced with other mammalian subjects, including humans, as well.

As will be shown by the data herein, several purine derivatives have been found to work effectively in accordance with the teachings of the present invention. In particular, the data shows that guanosine appears to work well in stimulating the production of neurotrophic factors and enhancing neuritogenesis. Similarly another exemplary purine derivative, 4-(3-(1,6-dihydro-6-oxo-9-purin-9-yl)-1-oxopropyl)amino) benzoic acid (AIT-082) has been shown to stimulate the in vivo activation or derepression of naturally occurring genes and the resultant production of naturally occurring genetically encoded molecules such as neurotrophic factors; and to increase neuritogenesis, enhance the effects of neurotrophic factors and alter the membrane potential of neurons thereby facilitating long term potentiation of the cells. AIT-082 is disclosed in U.S. Pat. No. 5,091,432 issued Feb. 25, 1992 to a co-inventor of the present application and incorporated herein by reference. Yet another exemplary composition which has been shown to be suitable for use in the present invention is inosine pranobex or isoprinosine. Inosine pranobex, a mixture of inosine and DIP-PacBa at a 1:3 molar ratio was found to enhance neuritogenesis and the effects of neurotrophic factors in vitro. The different embodiments of the present invention presented above demonstrate the applicability of using various purine derivatives to modify neural activity through modulating the carbon monoxide dependent guanylyl cyclase system.

Exemplary preferred embodiments of the methods of the present invention involve the treatment of cells or neurons with AIT-082 or 4-(3-(1,6-dihydro-6-oxo-9-purin-9-yl)-1-oxopropyl)amino) benzoic acid. AIT-082 is a unique derivative of the purine hypoxanthine containing a para-aminobenzoic acid moiety. It is rapidly absorbed after oral administration and, after crossing the blood brain barrier, enters the brain unchanged. It may be detected at levels as high as 3.3 ng/mg brain tissue 30 minutes after oral administration. AIT-082 induces the in vivo genetic expression of naturally occurring genetically encoded molecules including neurotrophic factors. As a result, it directly administers these compounds to the treated cells and stimulates neurite outgrowth from neuronal cells when added alone to the cultures as well as enhancing the neurotogenic effects of neurotrophic factors such as nerve growth factor (NGF). More importantly, AIT-082 enhances working memory in old, memory deficient mice after intraperitoneal and oral administration. The neurotogenic activity of AIT-082 is inhibited by hemoglobin, by Methylene Blue, and by ZnPP, all scavengers of CO, but not by CuPP or by other inhibitors of nitric oxide synthase. Screening tests for in vitro activity at known neurotransmitter and neuromodulator receptors were negative.

A further understanding of the present invention will be provided to those skilled in the art from the following non-limiting examples which illustrate exemplary protocols for the identification, characterization and use of purine derivatives in accordance with the teachings of the present invention.

EXAMPLE 1

Plasma Levels of AIT-082 in Mice

Adult C57BL/6 mice were administered 30 mg/kg of AIT-082 in saline i.p. The animals were sacrificed by decapitation at 30, 45, 60 and 90 minutes after administration of AIT-082. Blood was collected in heparinized tubes, mixed and centrifuged at 2000 rpm for 15 minutes. The plasma supernatant was removed and stored at −70° C. until analysis. A high pressure liquid chromatography system was developed for the analytical measurement of AIT-082 in plasma and brain tissue. The assay developed was selective for AIT-082 in the presence of a number of closely related purine molecules. The sensitivity of the method was 0.1 microgram of AIT-082 per ml of plasma and 0.1 microgram of AIT-082 per milligram of brain tissue (wet weight).

The results of these determinations are shown in Table A and graphically represented in FIG. 1 where plasma levels of AIT-082 are provided at 30, 45 and 60 minutes after administration of 30 mg/kg i.p. to C57BL/6 mice. From the data, it was estimated that the blood level of AIT-082 reached its peak at approximately 45 minutes and a plasma elimination half-time of approximately 12 minutes with the kel=3.45 hr-1.

TABLE A

Plasma Levels of AIT-082

| Time (min) | Level ($\mu$g/ml ± S.E.) |
|---|---|
| 15 | 42 ± 6 |
| 30 | 108 ± 13 |
| 45 | 437 ± 131 |

TABLE A-continued

Plasma Levels of AIT-082

| Time (min) | Level ($\mu$g/ml ± S.E. |
|---|---|
| 60 | 86 ± 24 |
| 90 | 20 ± 12 |

EXAMPLE 2

AIT-082 Crosses the Blood Brain Barrier

Brain tissue was analyzed from two animals receiving 30 mg/kg i.p. of AIT-082 and sacrificed 30 minutes after drug administration. The brains were rapidly removed and chilled on ice. Brain tissue was dissected into cortex and remainder of the brain. Brain tissue (approx. 250–300 mg wet weight) was homogenized with 5.0 ml of saline using a Brinkman Polytron tissue grinder and stored at −70° C. until analysis. Brain homogenates were deproteinized by ultrafiltration through Gelman Acrodisc filters; first through a 1.2 micron filter and then through a 0.2 micron filter. A 30 ml sample was injected into the HPLC for analysis as above. A standard curve was prepared by the addition of known quantities of AIT-082 to brain homogenates from untreated animals. Analysis of the brain tissue indicated that AIT-082 was detected in both the cortex sample and the remaining brain samples from both animals. The results are shown directly below in Table B.

TABLE B

Brain Tissue Levels of AIT-082

| Sample # | Brain Region | Brain wt (mg) | Level of AIT-082 (ng/mg brain tissue) |
|---|---|---|---|
| S3 | Cortex | 181 | 2.8 |
| S3 | Remainder | 153 | 3.3 |
| S4 | Cortex | 146 | 3.4 |
| S4 | Remainder | 217 | 2.3 |

This demonstration of the presence of AIT-082 in the brain tissue after 30 minutes is critical in that it indicates that AIT-082 crosses the blood-brain barrier without degradation.

EXAMPLE 3

AIT-082 Interacts with the Cholinergic System

Because of the finding that there is a severe loss of cholinergic neurons in the hippocampus in Alzheimer's disease patients, there has been considerable interest in the effect on memory of compounds which alter the activity of this system. Support for the cholinergic hypothesis of memory comes from studies using lesions or a stroke model. Lesions of the CA1 region of the hippocampus appear to specifically disrupt working memory. In the stroke model, occlusion of the vertebral and carotid arteries (30 minutes) produces specific cell loss in the CA1 region of the hippocampus and a loss of working memory. In these models in aged rats, physostigmine, a cholinesterase inhibitor, has been shown to improve memory. THA, another drug which increases cholinergic function, was shown to improve memory in aged monkeys. The observation that AIT-082 improves memory in the same general manner as physostigmine and THA raises the question of whether AIT-082 might have some effect on the cholinergic system.

To elucidate the mechanisms by which AIT-082 improves memory, attempts were made to block its actions by co-administration of the short-acting cholinergic antagonist atropine to mice and subjecting them to simple learning tests. Atropine reportedly has the ability to block the effects of physostigmine and THA. Mice were injected with AIT-082 (30 mg/kg) 2 hr prior to testing on days 1 through 4. Atropine (0.5 mg/kg) (28), was injected ½ hour prior to testing or 1.5 hours after AIT-082 on day 3 only. All injections were i.p. After a reference run to determine where the reward was placed in a T-maze, the mice were retested to determine if they could remember the location of the reward. The percentage of correct responses is graphically represented in FIG. 2.

Figure 2:
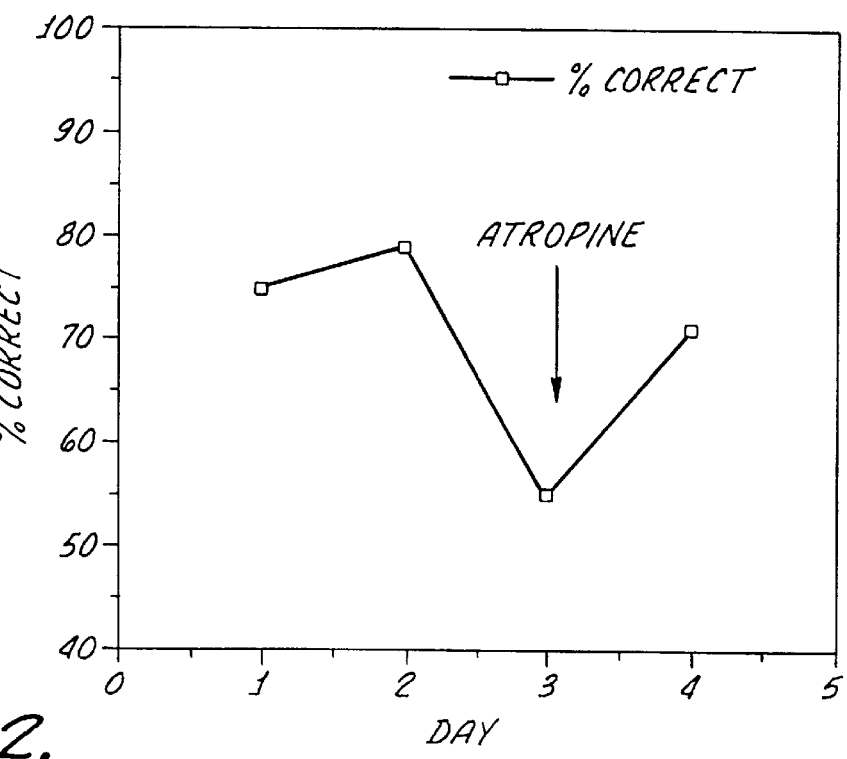
FIG. 2 is a graphical representation of the effect of atropine, a cholinergic antagonist, on memory enhancement in mice by the purine derivative AIT-082.

FIG. 2 demonstrates that atropine blocked the memory enhancing activity of AIT-082 on day 3 and that the effect was transient since the enhancing effects of AIT-082 reappeared on day 4 when no atropine was administered. This observation suggests that a cholinergic mechanism may be involved in the action of AIT-082.

EXAMPLE 4

Effect of AIT-082 on Acetylcholine Receptors

The interaction of AIT-082 with acetylcholine receptors was determined by interference with the binding of QNB (3-quinuclidinyl benzilate) in mouse tissue using the method of Fields (J.Biol. Chem. 253(9): 3251–3258, 1978). There was no effect of AIT-082 in this assay.

In the study, mice were treated with AIT-082 at 30 mg/kg 2 hours prior to sacrifice, decapitated and the tissue processed to obtain membranes containing the acetylcholine receptors. When these tissues were assayed in vitro, there was no effect of AIT-082 on affinity (Kd) for QNB when AIT-082 was administered under the same conditions as utilized in testing for effects on memory. There was a change in the number of receptors (B max) in cortex and striatum, with the cortex showing a decrease and the striatum an increase in acetylcholine binding sites. These data are consistent with the hypothesis that there is an increase input to the cortex as a result of AIT-082 being administered to the animals. Typically, an increased input will result in down regulation of the receptors.

EXAMPLE 5

Effect of AIT-082 on Receptor Ligand Binding in Vitro

AIT-082 was evaluated for its ability to inhibit ligand binding to 38 isolated receptors. The receptors screened and their ligands were:

Adenosine

Amino Acids:
  Excitatory Amino Acids (glycine, kainate, MK-80 1, NMDA, PCP, quisqualate and sigma);
  Inhibitory Amino Acids (benzodiazepine, GABA-A, GABA-B, and glycine)

Biogenic Amines (dopamine-1, dopamine-2, serotonin-1, serotonin-2)

Calcium Channel Proteins (nifedipine, omegaconotoxin, chloride, potassium)

Peptide Factors (ANF, EGF, NGF)

Peptides: (angiotensin, arg-vasopressin-V1 and V2, bombesin, CCK central and peripheral, neurotensin, NPY, somatostatin, substance K, substance P, VIP)

Second Messenger Systems:
  Adenyl Cyclase
  Protein Kinase (phorbol ester and inositol triphosphate)

The testing was conducted under contract at Nova Labs (Baltimore, Md.). AIT-082 had no activity in any of the in vitro assays conducted.

Accordingly, while AIT-082 acts through the cholinergic nervous system (atropine blocks its activity), AIT-082 appears to act through a mechanism that does not involve direct interaction with acetylcholine receptors. It is of importance to note that in vitro, AIT-082 does not bind to the adenosine receptor.

AIT-082 was evaluated in a series of psychopharmacological tests that were established in order to more fully evaluate the scope of its central nervous system activity. Among the tests utilized were:

(a) motor coordination, by the accelerating Rota-Rod treadmill, (b) exploratory and home cage locomotor activity, by the Stoelting activity monitor, (c) anxiolytic activity, by the elevated Plus maze, and (d) nocioception.

AIT-082 was compared with standard reference drugs.

EXAMPLE 6

AIT-082 Increases Motor Coordination in Mice

Motor coordination was measured using an accelerating Rota-Rod treadmill for mice (Ugo Basile Co.). At various times after treatment with saline or drug, mice were placed on the Rota-Rod, which accelerates to maximum speed over a 5 minute period. The time in seconds at which the subject falls off was recorded in Table C directly below. Each animal was tested 3 times and the mean time was recorded.

TABLE C

Effect of AIT-082 on Roto-rod performance

| AIT dose (mg/kg) | Time (sec) |
|---|---|
| Control | 123 ± 64 |
| 0.005 | 162 ± 93 |
| 0.05 | 207* ± 73 |
| 0.5 | 184* ± 76 |
| 30.0 | 187* ± 68 |
| 60.0 | 229* ± 80 |

*$p < 0.05$, t-test vs controls

Subjects receiving AIT-082 showed improved motor coordination by remaining on the roto-rod for longer periods of time when compared to control (saline) or low doses (0.005 mg/kg).

EXAMPLE 7

AIT-082 Does Not Inhibit Exploratory Activity

To measure exploratory behavior, subjects received saline or AIT-082 administration, were placed in a novel large cage (25×48×16 cm, W×L×H), and movement was measured at one-minute intervals for 30 minutes. The large cage (San Diego Instruments, San Diego, Calif.) was equipped with vertical detectors and rearing movements were also recorded. No effects were noted with respect to exploratory activity indicating that the subjects were not incapacitated.

EXAMPLE 8

AIT-082 Does Not Inhibit Locomotor Activity

To measure home cage locomotor activity, the home cage was placed on a platform of an activity monitor (Stoelting Instruments). Home cage locomotor activity movements were recorded at one minute intervals for 15 minutes. Subjects received saline or AIT-082 and were returned to their home cages. Ten minutes after injection, the home cage was re-placed on the platform of the activity monitor. Home cage locomotor activity movements were recorded at one minute intervals for 30 minutes. During the first five minutes, grooming activity was also monitored and recorded. The results are shown in Table D directly below.

TABLE D

Effect of AIT-082 on locomotor activity

| AIT dose (mg/kg) | Movements (mean ± S.D.) | | |
|---|---|---|---|
|  | Pre-drug | Post-drug | Difference |
| Control | 1633 ± 434 | 1385 ± 492 | 248 ± 492 |
| 0.005 | 1884 ± 230 | 1375 ± 563 | 509 ± 429 |
| 0.05 | 1718 ± 606 | 1508 ± 456 | 209 ± 340 |
| 0.5 | 1610 ± 349 | 1320 ± 689 | 290 ± 435 |
| 30.0 | 1440 ± 264 | 1098 ± 189 | 342 ± 267 |
| 60.0 | 1690 ± 223 | 634* ± 223 | 1056* ± 154 |

*$p < 0.05$, t-test vs controls

As shown by the data in Table D, at the high dose (60 mg/kg), subjects may have become more habituated to their environment and exhibited less movement after treatment with AIT-082. Otherwise, no effects were noted.

EXAMPLE 9

AIT-082 Does Not Substantially Increase Anxiety

A Plus maze was constructed of black plexiglass consisting of two opposite-facing open arms (30×5 cm, L×W) and two opposite facing closed arms (30×5×15 cm, L×W×H). The walls of the closed arms were clear plexiglass and the four arms were connected by a central area 5×5 cm. The entire Plus maze was mounted on a base 38 cm above the floor. Testing consisted of placing the subject at one end of one of the open arms. The time the subject took to leave the start position (the first 10 cm of the open arm) was recorded. The time it took for the subject to enter halfway into one of the closed arms was also recorded. When the subject arrived at the half-way point in the closed arm, the three-minute test session began. During the three-minute test session, the number of times the subject entered the open arms was recorded. An entry was defined as placing at least two paws onto the platform of the open arm. There was a slight anxiogenic effect of AIT-082 at 30 mg/kg, but this was not observed at a higher dose (60 mg/kg) or at the lower doses (0.005 to 0.5 mg/kg).

EXAMPLE 10

AIT-082 Does Not Effect Nocioception

Mice were placed on an electric hot plate (Omnitech) at 55° C. and the latency time until the subject licked his hind paw was measured. If there was no response by 45 seconds, the trial was terminated. By this test there was no effect of AIT-082 on nocioception.

EXAMPLE 11

AIT-082 Is Not Toxic

Preliminary acute toxicity tests in rats and mice of AIT-082 have demonstrated that the LD50 is in excess of 3000 mg/kg when administered by the oral or intraperitoneal route. AIT-082 has been evaluated under Panlabs's General Pharmacology Screening Program (Panlabs, 11804 North Creek Parkway South, Bothwell, Wash. 98011) and the results indicated an absence of any toxicity when measured in their standard profile of 79 different test systems.

By the nature of the chemical structure of AIT-082, it is not anticipated that the compound will be metabolized into any toxic metabolites.

In conclusion, there were few deleterious effects of AIT-082 on a variety of psychopharmacological tests except for a slight anxiogenic effect at one dose. There was an increase in motor coordination (roto-rod test) over a range of doses (0.05 to 60 mg/kg) and possibly a learning or habituation effect at one dosage (60 mg/kg) in the locomotor test.

Following psychopharmacological characterization of this exemplary compound, further studies were conducted to demonstrate the neurogenic effects of the present invention.

EXAMPLE 12

AIT-082 Promotes Neuritogenesis in PC12 Cells

Much of the work performed in the characterization of the compounds of the present invention involved the use of PC12 cells. These cells are derived from a rat pheochromocytoma and when grown in the presence of NGF, extend neurites, cease cell division and assume many characteristics of sympathetic neurons. When cultured in the absence of nerve growth factor (NGF), few PC12 cells have neurites greater than one cell diameter. Addition of saturating concentrations of NGF for 48 hours stimulates neurite outgrowth in about 20–35% of the cells. Because they constitute a homogeneous population of neuronal-like cells, without contaminating astroglia type cells, it is possible to study the direct effects of the purine based compounds on neurite outgrowth in these cells.

To demonstrate neuronal modification by the exemplary compounds of the present invention, a dose response curve of AIT-082 was generated measuring the stimulation of neuritogenesis in PC12 cells. Cells cultured in RPMI 1640 with 1.5% horse serum and 1.5% fetal bovine serum were re-plated onto poly-ornithine coated 24-well culture plates ($2.5 \times 10^4$ cells per well). AIT-082 and NGF were added to the various cultures immediately upon plating. After 48 hours, medium was removed and the cells immediately fixed in 10% formalin and PBS for 10 minutes. Cells and neurites were counted within 2 days of fixation.

A neurite was defined as a process extending from the cell at least 1 cell body diameter in length and displaying a growth cone at its tip. For each treatment, 2 representative microscope fields were counted from each of 6 sister cultures receiving identical treatments. The total number of cells counted per well (approximately 100 cells) and the total number of cells containing neurites in each well were used to determine fraction of neurite-bearing cells. The mean values (±SEM) were then determined for each of the treatments. To facilitate comparison neurite outgrowth was expressed relative to the proportion of cells bearing neurites in the presence of NGF alone (NGF=100%). The effects of compounds with and without NGF were compared by analysis of variance (ANOVA) followed by Tukey's test for significance.

Figure 3:
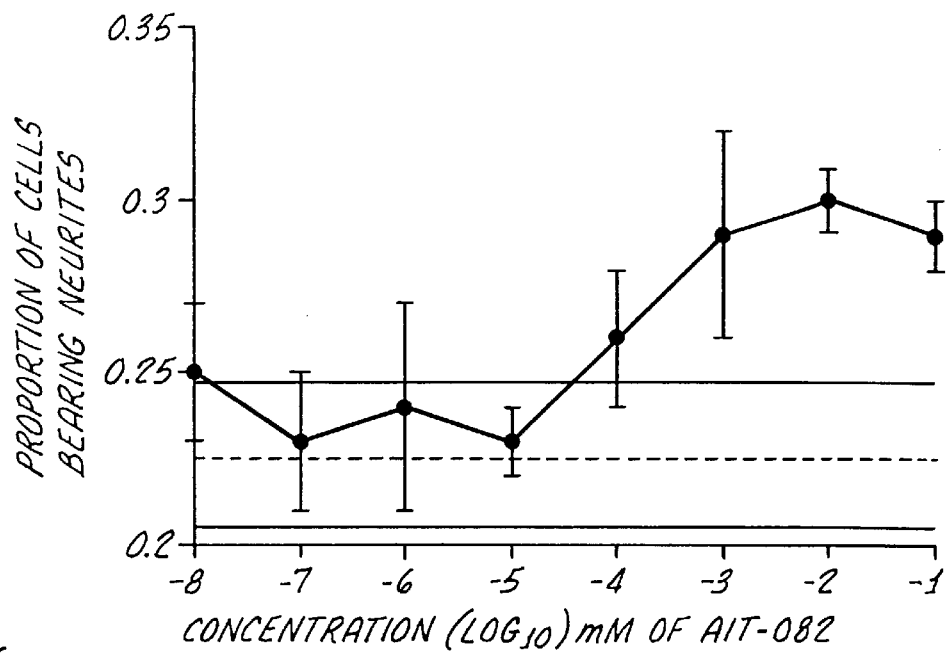
FIG. 3 is a graphical representation of nerve growth factor mediated neurotogenic response in neuronal cells grown in vitro with various concentrations of the purine derivative AIT-082.

The results are shown in FIG. 3 where the curve represents different levels of AIT-082 plus saturating concentrations (40 ng/ml) 2.5 S NGF. The center horizontal line represents control values for cells cultured in the presence of 40 ng/ml NGF alone. Upper and lower horizontal lines are indicative of confidence limits of NGF alone as determined using standard statistical methods.

As shown in FIG. 3, AIT-082 stimulates neuritogenesis and enhances NGF-stimulated neuritogenesis in PC12 cells at low concentrations (1 mM). Analysis of the data shows that AIT-082 was as effective as NGF in promoting neuritogenesis in PC12 cells and enhanced the optimal effects of NGF by 30%. For the purposes of comparison, and as will be discussed in more detail below, inosine and hypoxanthine are weakly effective in stimulating neuritogenesis and in enhancing NGF-stimulated neuritogenesis in PC12 cells but are effective at lower concentrations of 30–300 nM. Guanosine produces a significant effect similar to AIT-082 but at a higher concentration of 30–300 mM.

EXAMPLE 13

Effect of Inhibitors on AIT-082 Neutritogenesis

Age-related memory loss has been associated with loss of NGF-dependent basal forebrain neurons. It can be ameliorated by i.c.v. infusion of NGF. The effect of AIT-082 on neuritogenesis alone and with NGF were studied using the protocol of Example 12. In order to study the mechanism by which AIT-082 exerts its effects, a series of experiments were conducted in which inhibitors were utilized to block or modify specific biochemical processes. All of the cultures contained NGF at optimal dose (40 ng/ml) so the series without AIT-082 added represented the effect of the inhibitors on NGF activity. Where indicated, AIT-082 was added at 10 mM, its apparent, presently understood, optimal dose. Three selective inhibitors were used.

Figure 4A:
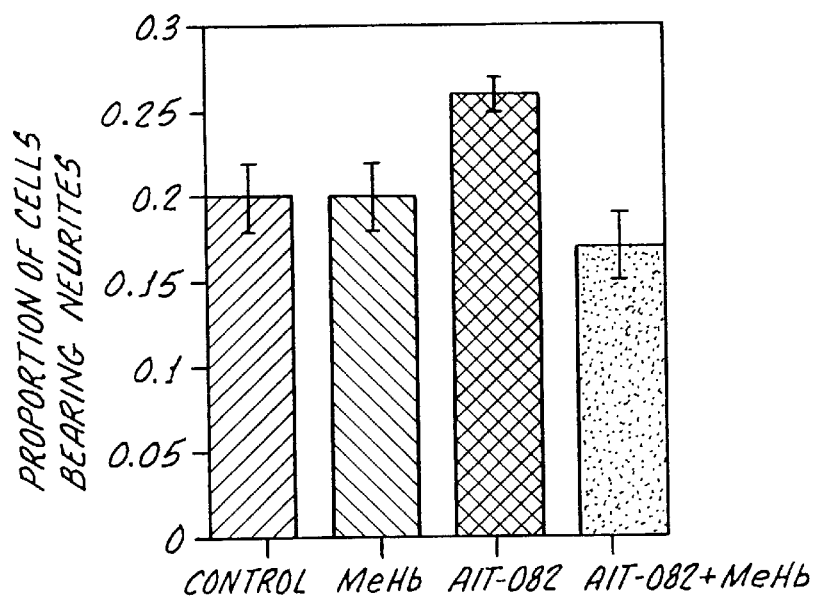
FIGS. 4A, 4B and 4C are graphical comparisons of the effects of selective inhibitors and the purine derivative AIT-082 on nerve growth factor mediated neurotogenic response.
Figure 4B:
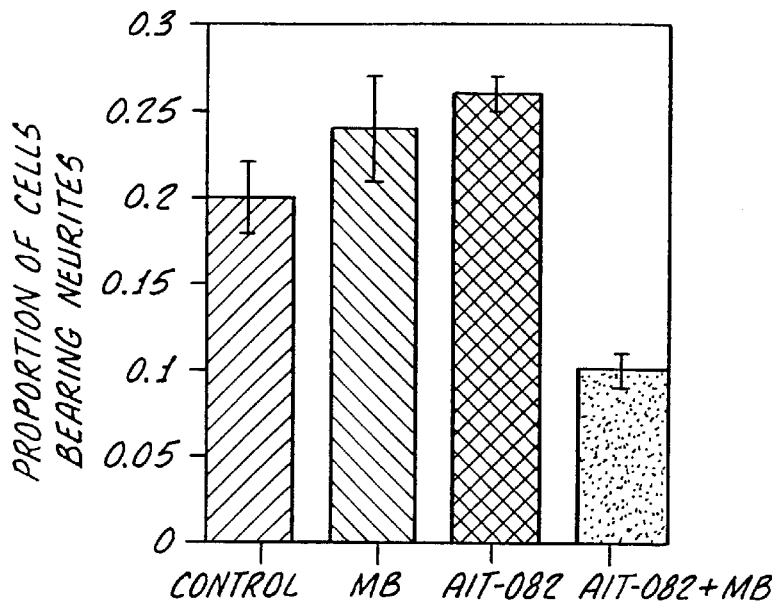
Figure 4C:
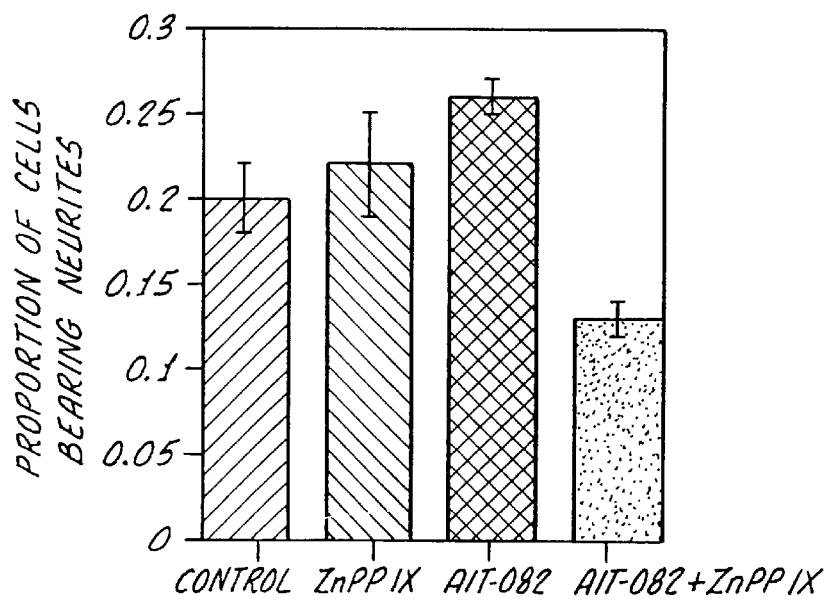

The results of these studies are shown below in Table E below, and FIGS. 4A, 4B, and 4C graphically present the proportion of cells bearing neurites after 48 hours culture under the conditions indicated. The base line value was cells grown without NGF or AIT-082.

TABLE E

Effect of AIT-082 and selective inhibitors on neuritogenesis alone and with NGF

| Inhibitor | Concentration | AIT-082 alone[1] | NGF alone | AIT-082 + NGF |
|---|---|---|---|---|
| None |  | 0.2 ± 0.02 | 0.2 ± 0.02 | 0.26 ± 0.01 |
| Methemoglobin | 0 |  | 0.2 ± 0.02 | 0.26 ± 0.01 |
|  | 1 μM |  | 0.2 ± 0.02 | 0.17 ± 0.02 |
| Methylene Blue | 0 |  | 0.2 ± 0.02 | 0.26 ± 0.01 |
|  | 5 μM |  | 0.24 ± 0.03 | 0.10 ± 0.01 |
| Zn Protoporphyrin IX | 0 |  | 0.20 ± 0.02 | 0.26 ± 0.01 |
|  | 1 μM |  | 0.22 ± 0.03 | 0.13 ± 0.01 |

[1]Proportion of cells bearing neurites

Methemoglobin Nib) captures and removes nitric oxide (NO) and carbon monoxide (CO) from the culture media. MHb had no effect on NGF activity but inhibited the action of AIT-082, implying that either NO or CO is involved in the action of AIT-82.

Methylene blue (MB) inhibits soluble guanylyl cyclase, the enzyme which produces cyclic GMP (cGMP) an intracellular substance which, as previously discussed, is involved in the second messenger system of nerve impulse transmission. MB had no effect on NGF activity but inhibited the action of AIT-082, implying that guanylyl cyclase is involved in the mechanism of action of AIT-082.

Zinc protoporphyrin IX (ZPP) is an inhibitor of heme oxygenase 2, which produces carbon monoxide. ZPP had no effect on NGF activity but inhibited the action of AIT-082, implying that the production of carbon monoxide is involved in the mechanism of action of AIT-082.

EXAMPLE 14

Effect of Nitric Oxide Inhibitors on AIT-082

Figure 5A:
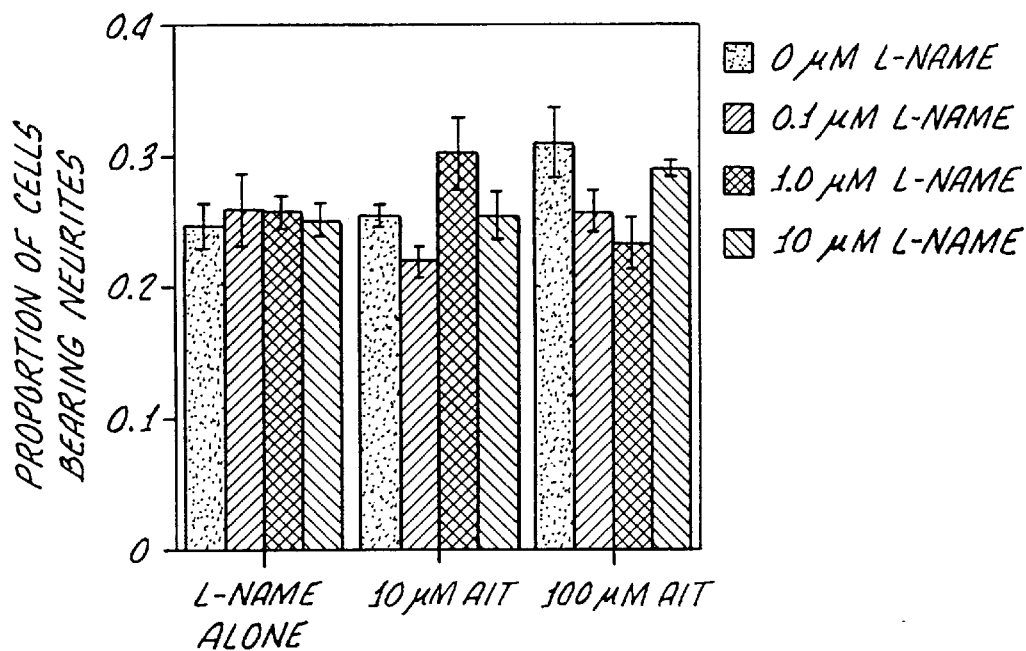
FIGS. 5A and 5B are graphical comparisons of nerve growth factor mediated neurotogenic response for cells grown in the presence of the purine derivative AIT-082 and various concentrations of nitric oxide inhibitors.
Figure 5B:
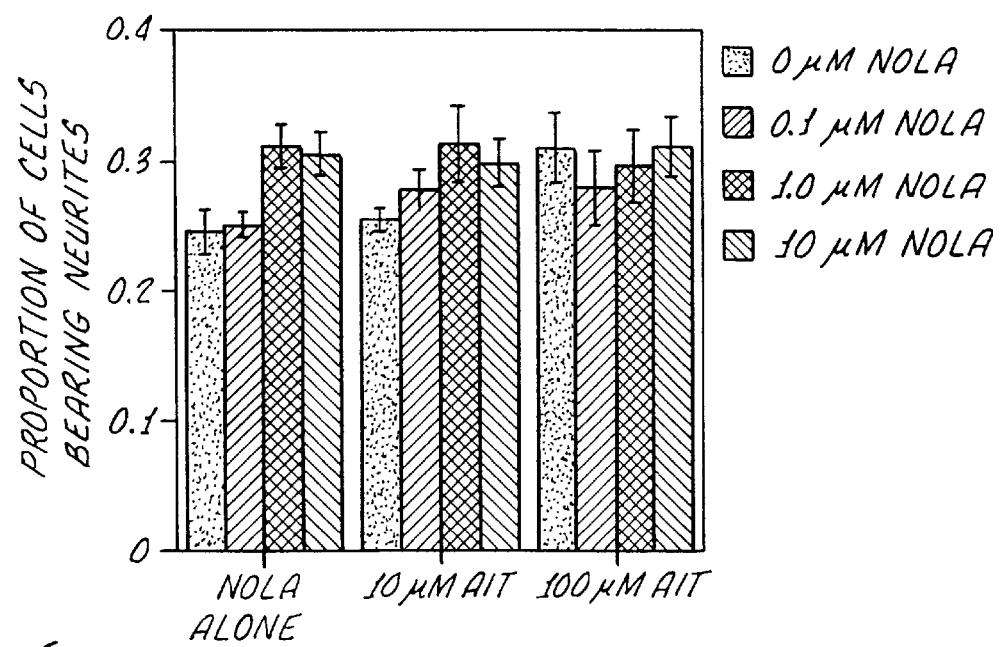

Nitric oxide is produced by the action of the enzyme nitric oxide synthetase (NOS). Two chemicals that have been shown to selectively inhibit NOS are N-nitro-L-arginine methyl ester (L-NAME) and N-nitro-L-arginine (NOLA). Different levels of these chemicals were administered simultaneously with AIT-082 and neuritogenesis in PC12 was measured using the protocol of Example 12. The results for L-NAME are presented in Table F while the results for NOLA are presented in Table G. Both tables are shown directly below with graphical representations of the data presented in FIGS. 5A and 5B.

TABLE F

The effect of L-NAME on neuritogenesis

| AIT-082 | Concentration of L-NAME ($\mu$M) | | | |
|---|---|---|---|---|
| | None | 0.1 | 1.0 | 10.0 |
| 0 | 0.246 ± 0.017 | 0.259 ± 0.027 | 0.257 ± 0.013 | 0.251 ± 0.013 |
| 10 $\mu$M | 0.254 ± 0.008 | 0.220 ± 0.010 | 0.302 ± 0.027 | 0.254 ± 0.018 |
| 100 $\mu$M | 0.309 ± 0.027 | 0.257 ± 0.016 | 0.232 ± 0.019 | 0.289 ± 0.006 |

TABLE G

The effect of NOLA on neuritogenesis

| AIT-082 | Concentration of NOLA ($\mu$M) | | | |
|---|---|---|---|---|
| | None | 0.1 | 1.0 | 10.0 |
| 0 | 0.246 ± 0.017 | 0.259 ± 0.009 | 0.311 ± 0.016 | 0.305 ± 0.017 |
| 10 $\mu$M | 0.254 ± 0.008 | 0.277 ± 0.016 | 0.312 ± 0.029 | 0.298 ± 0.019 |
| 100 $\mu$M | 0.309 ± 0.027 | 0.279 ± 0.027 | 0.295 ± 0.028 | 0.310 ± 0.023 |

As shown by the data in Tables F and G, neither of these inhibitors of NOS were active in blocking the effect of AIT-082 on neuritogenesis. These results indicate that NO was not involved in the mechanism of action of AIT-082.

EXAMPLE 15

Effect of AIT-082 on cGMP Levels in PC-12 Cells

To demonstrate CO-dependent guanylyl cyclase modification, cyclic guanosine monophosphate (cGMP) levels in PC12 cells were measured following addition of AIT-82. Initially, PC-12 cells were primed with 40 ng/ml NGF for 3 days in low serum medium (1.5% horse serum +5% fetal calf serum). Cells were seeded onto assay plates in low serum medium containing 40 ng/ml NGF and incubated for 1 hour. The medium was changed to low arginine medium (80 $\mu$M) with no serum and NGF and papaverine (100 mM) where indicated. Test compounds were added for the indicated time and the reaction was stopped by adding 5% TCA containing 10,000 dpm of $^3$H-cGMP. cGMP was assayed by the radioimmunoassay method of Maurice (Mol. Pharmacol. 37: 671–681, 1990). TCA was purified by adding powdered charcoal (5 g) and filtering the mixture through Whatman #1 paper. This removed contaminants in the TCA that otherwise interfere with the radioimmunoassay (RIA) of cGMP.

It was necessary to purify the cGMP from cAMP and other contaminants before radioimmunoassay since these other materials can interfere with the assay. Briefly, the TCA solution was applied to Dowex columns (50W-8X, 200–400 mesh) and eluted. A neutral alumina column was then placed under each Dowex column. The cGMP was eluted from the Dowex columns into neutral alumina columns by adding 4 mL of 0.05M HCl to each Dowex column. The neutral alumina columns were then sequentially rinsed with 2 ml of HCl, 4 mL water and finally with 0.2M sodium acetate (pH 6.2). The cGMP collected for the RIA, eluted in 1 mL of sodium acetate with a recovery between 50–65%. The cGMP was assayed using a Dupont RIA kit. The results are graphically presented in FIG. 6.

Figure 6:
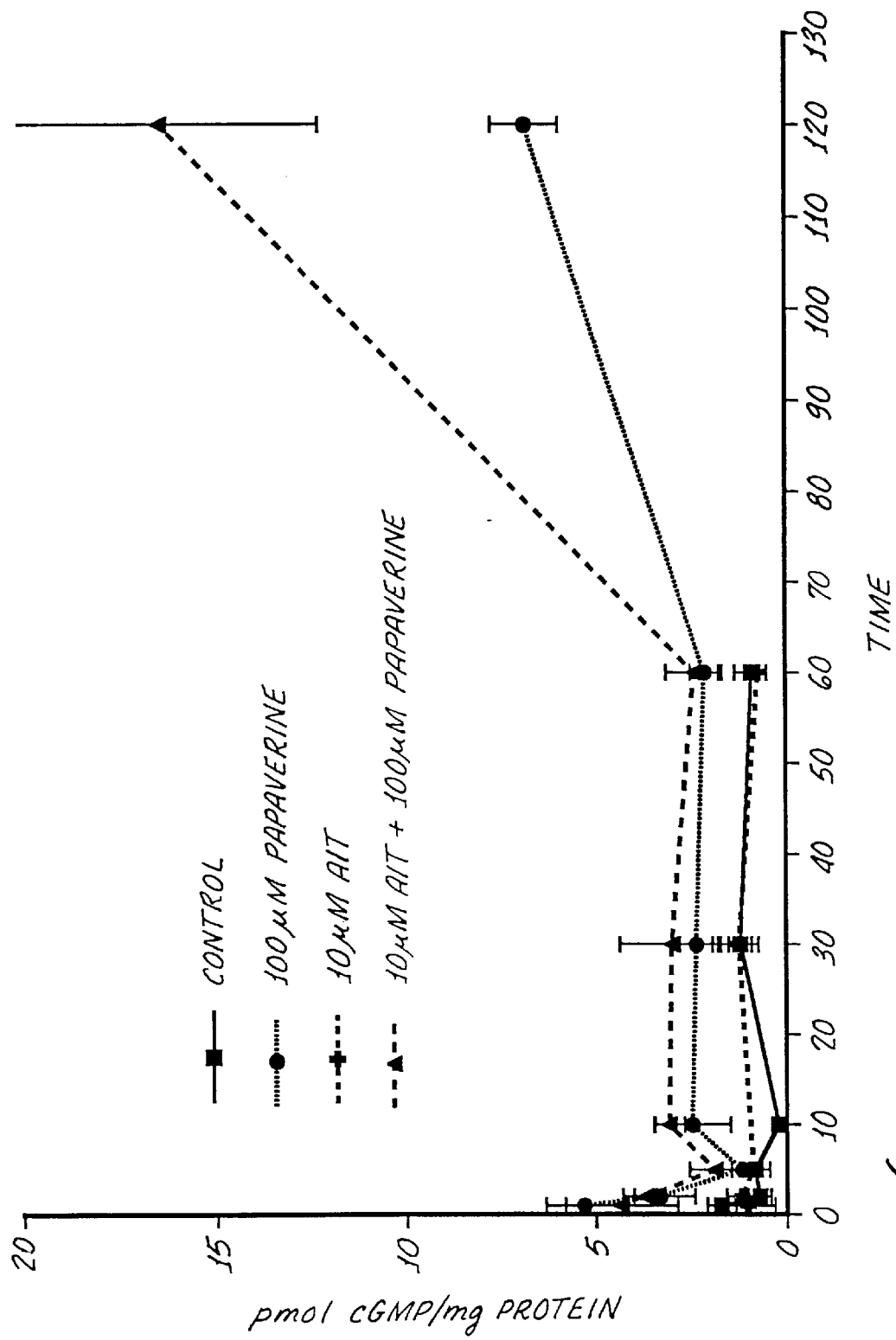
FIG. 6 is a graphical comparison of cyclic GMP production in neuronal cells grown in culture with the purine derivative AIT-082 and without AIT-082.

As shown in FIG. 6, the addition of AIT-082 increased the production of cGMP in PC12 cells indicating that AIT-082 acts by modifying the activity of the carbon monoxide-dependent enzyme guanylyl cyclase.

EXAMPLE 16

Effect of AIT-082 on Genetic Expression of Neurotrophin mRNA

To demonstrate that AIT-082 induced the in vivo genetic expression and resultant cellular production of neurotrophins, naturally occurring, genetically encoded molecules, as well as enhancing their activity, the following experiment was performed. Induction of neurotrophin mRNA was determined by northern blot analysis of astrocytes cultured with AIT-082, NGF, or both. The cells were harvested and RNA extracted at 24 hours after treatment.

More particularly, astrocytes from the cerebral cortex of NIH Swiss mice (Harlan) were isolated. Briefly, newborn pups (0–24 hours) were decapitated. Their brains were removed under aseptic conditions and were placed in modified Dulbecco's medium (DMEM) containing 20% heat-inactivated horse serum (Hyclone)—("complete medium"). The neopallium was then dissected from each cerebral hemisphere and minced into 1 mm cubes.

The astrocytes were then isolated by mechanical dissociation. The cubes were vortexed at maximum speed for one minute. The cell suspension was then passed first through 75 mm Nitex then through 10 mm Nitex. The resulting cell suspension was diluted in complete medium to a final concentration of one brain per 10 ml of complete medium. Ten milliliters of the diluted cell suspension, was added to each 100 mm Falcon tissue culture plate (Fisher). After 3 days the medium was replaced with 10 ml fresh complete medium and subsequently was replaced twice weekly with DMEM containing 10% heat inactivated horse serum—("growth medium"). After two weeks in culture the astrocytes formed a confluent monolayer.

For RNA extraction, astrocytes were trypsinized. The astrocytes were then replated onto 100 mm PORN coated plates at a cell density of 106 cells per plate (10 ml growth medium). After 2 hrs PBS, Guo, or GTP at 10 mM were added to the appropriate plates. Total RNA was harvested from 1.5×107 cells for each treatment, 4 and 24 hrs after treatment using TRIzol reagent and supplier protocol (GIBCO BRL/Life Technologies, Inc.). For slot blots, total RNA was bound to Hybond-N filters (Amersham/United States Biochemicals) as described in *Transfer and Immobilization of Nucleic Acids and Proteins to S & S Solid Supports* (S and S protocols: Schleicher & Schuell, New Hampshire, USA). Northern blots were also performed using 10–20 mg total RNA from each sample. These were electrophoresed in 1% agarose gels containing formaldehyde and blotted onto Hybond-N filters according to S and S protocols.

The blots were probed with $P^{32}$-labelled cDNA (NGF, NT-3 and BDNF probes) or oligonucleotide probe (FGF-2) by hybridization in Piperazine-N,N'-bis-(2-ethanesulfonic acid) (PIPES) buffer (50 mM PIPES, pH 6.8; 50 mM NaH2PO4; 0.1 M NaCl; 5%SDS and 1 mM EDTA) overnight at 50° C. The blots were then washed twice with (2×SSC, 0.1%SDS) wash buffer at room temperature for 20 minutes each, and then with (0.1×SSC, 0.1%SDS) wash buffer twice at 52° C. for 20 minutes each. 1×SSC is 0.15M NaCl and 15 mM sodium citrate, pH 7.0. Damp membranes were wrapped in Saran wrap and autoradiography was performed using Hyperfilm-ND (Amersham/USB) and a cassette with intensifying screens. Various concentrations (0.25 to 4 mg of total RNA), as determined by spectrophotometry, of each sample were blotted and probed so that quantification could be done after insuring a linear film response. Quantification was performed using MCID Image Analysis (St. Catherine's, Ontario, Canada).

To provide probes, a cDNA clone of the mouse NGF gene in the plasmid pGEM.NGF(+), and cDNA clones of human NT-3 and BDNF in Bluescript were isolated. After isolation, the cDNA probes were labeled with 32P-dCTP (ICN Biomedicals Canada, Ltd.) using a Random Primed DNA Labeling Kit (Boehringer Mannheim Biochemica) as described in the kit.

A 40-mer antisense oligonucleotide was synthesized (MOBIX, McMaster University) as a probe for FGF-2. This was complementary to the 5' end of mouse FGF-2 coding sequence on the mRNA. The oligo was 5' end-labeled using polynucleotide kinase, One-Phor-All buffer, and the protocol supplied by Pharmacia Biotech Inc., and ATPgP32 (ICN Biomedicals Canada, Ltd.).

The results of the study for the production of four different neurotrophic factors are shown below in Table H.

TABLE H

Northern Blot analysis of neurotrophin mRNAs from Astrocytes

| Neurotrophin mRNA | Control | NGF 40 ng/ml | AIT-082 100 mM | AIT-082 (100 mM) + NGF (40 ng/ml) |
|---|---|---|---|---|
| NGF | – | – | ++ | + |
| FGF-2 | + | – | ++ | + |
| BDNF | + | + | + | + |
| NT-3 | – | – | ++ | + |

The conditions which produced a detectable amount of each of the neurotrophin mRNAs are indicated by a "+", with a "++" indicating that at least twice the detectable amount was present. Those blots which were negative are indicated by a "–".

The results indicate that AIT-082 induced the expression of mRNAs for several neurotrophic factors, including NGF. More importantly, these data clearly establish that AIT-082 selectively and controllably induced the in vivo genetic expression of at least one naturally occurring genetically encoded molecule in a mammal treated in accordance with the teachings of the present invention. Administering this exemplary purine derivative selectively induced the expression of mRNA encoding three of the four identified neurotrophic factors, NGF, FGF-2, and NT-3, but did not induce activation or derepression of the gene encoding for BDNF mRNA. This selective control coupled with the ease of administration provided by the compounds and methods o the present invention effectively overcomes the limitations of the prior art. Rather than administering these molecular compounds directly to cells through complex and potentially dangerous techniques, the present invention is able to treat a mammalian patient utilizing traditional, noninvasive drug delivery routes that induce the treated cells to express the genetic material encoding the desired compounds resulting in their direct in vivo delivery and administration. Though potentially useful in conjunction with modified genes or other molecular biology techniques, with the present invention, genetic modification is unnecessary.

It has been shown previously that, within the hippocampus from Alzheimer's patients, there is an altered program of gene expression leading to aberrant levels of mRNA for neurotrophic factors. A number of animal and clinical studies have demonstrated that administration of single neurotrophins are inadequate to treat neurodegenerative disease. Accordingly, the ability of the compounds of the present invention to stimulate the production of multiple neurotrophin mRNAs within cells substantially increases their potential as treatments for a variety of neurodegenerative diseases by providing a method for the effective direct administration of these naturally occurring genetically encoded molecules to a patient through the induction of their in vivo genetic expression.

The preceding examples show that AIT-082 stimulates neuritogenesis in vitro in PC12 cells alone and enhances the effect of nerve growth factor (NGF). Further, the neurotogenic effect of AIT-082 was reduced by methemoglobin (which captures and removes nitric oxide and carbon monoxide), methylene blue (which inhibits guanylyl cyclase), and by zinc protoporphyrin IX (an inhibitor of heme oxygenase 2, which produces carbon monoxide). The neurotogenic effect of AIT-082 was unaffected by L-NAME or NOLA, inhibitors of NO production. In addition, AIT-082 stimulated the production of a number of different neurotrophic factors as evidenced by increased mRNA levels of these factors in astrocytes after AIT-082 administration in vitro. Moreover, since AIT-082 is orally active and rapidly passes the blood-brain barrier as shown in Example 2, it has significant therapeutic potential as an NGF-mimetic agent in Alzheimer's disease and in other neurodegenerative diseases.

In view of the previous results, studies were performed to demonstrate the effectiveness of using AIT-082 to treat neurodegenerative diseases. Loss of memory represents the core symptom of Alzheimer's disease as it does in a number of other neural afflictions. Specifically working (or episodic) memory is impaired in Alzheimer's disease, amnesia, aging and after hippocampal lesions in monkeys. The effects of AIT-082 in ameliorating this memory loss was used to demonstrate the efficacy of the compounds of the present invention with respect to the treatment of neurodegenerative diseases.

EXAMPLE 17

Comparison of Memory Trace in Different Mice Strains

The win-shift T-maze paradigm has been shown to specifically model working memory in rodents and is a widely accepted method. The rodent's natural behavior is to forage for food when hungry and therefore it will not return to the same location after it has consumed any food that was present. This model was not designed to account for all of the vast data on memory. Data from hypoxia and ischemia studies, procedures which selectively damage CA1 hippocampal cells, produce deficits in working memory while other types of memory are not affected. This strongly suggest that there are several types of memories which have different anatomical sites and most likely different neurochemical inputs. Accordingly, while the win-shift model may not account for all neurochemical inputs involved in working memory, the model does provide a useful art accepted tool in designing pharmacological experiments to provide information on the mechanism by which memory can be modified.

Male Swiss Webster mice six months (young adult) and eleven months (old) of age, obtained from the National Institute on Aging, were maintained in individual cages, on a 22 hour light/dark cycle with continuous access to water. Food was limited so that the mice stabilized at 80% of free feeding weight. Mice were weighed and handled daily for one week. The win-shift model was run as described in the literature and consists of a T-maze in which the correct response alternates after each correct trial. The interval between trials is varied and allows for the determination of the longest period between trials that a subject can remember the correct response on the previous trial. This allows the measure of the duration of the memory trace. A score of 5 (5 correct responses per 10 trials, 50% correct) is considered chance; that is, the animal does not remember which box it selected for positive reward on the previous trial. The reward goal box is alternated after each correct trial. Ten trials per mouse are run each day. If the animal establishes a spatial learning set (right side only), they would return to the same goal each trial and have a correct response rate of significantly less than 50% correct. The latency time to leave the start box is recorded as a measure of motivation, the running time (the time from leaving the start box to reaching the goal box) is recorded as a measure of performance, and the number of correct responses as a measure of memory.

The data in Table I illustrate the effect of increasing the inter-trial interval in young adult mice without any drug treatment.

TABLE I

Effect of inter-trial interval in win-shift paradigm[1]

| | Inter-trial Interval (seconds) | | | | |
|---|---|---|---|---|---|
| | 30 | 60 | 90 | 120 | 150 |
| Swiss Webster mice | 7.5* | 7.5* | 5.0 | | |
| C57BL/6 mice | 7.0* | 7.4* | 7.0* | 7.8 | 5.6 |

[1]Score is the mean number of correct responses per 10 trials. Saline was administered 1 hour prior to testing.
*p < 0.05. Data analysis following significant ANOVA, a Dunnett test was run comparing drug tested groups with controls. An Arc Sign transformation was performed on percentage data.

From the data in Table I, it can be seen that Swiss Webster mice are capable of remembering the win-shift strategy when the inter-trial delay interval is 30 or 60 seconds. Few mice with saline treatment scored above chance (50%) with the 90-second inter-trial delay interval. These data indicate that the "memory trace" in these animals disappears between 60 and 90 seconds All drug evaluation tests in normal adult Swiss Webster mice were conducted with the 90-second inter-trial interval except where indicated otherwise. In C57BL/6 mice, the duration of the memory trace was 120 seconds.

EXAMPLE 18

Effect of AIT-082 on Memory Trace Duration

The activity of AIT-082 was compared with tacrine (THA) and physostigmine (PHY), experimental anticholinesterase agents which enhance memory in animals. The drugs were also evaluated for their effects on locomotor activity. In the win-shift memory paradigm, AIT-082 was evaluated for its ability to induce tolerance after 18 days of drug administration. In addition AIT-082 was tested for its activity to modify learning in a modified T-maze discrimination task.

The drugs used in this example are 4-((3-(1,6-dihydro-6-oxo-9-purin-9-yl)-1-oxopropyl)amino) benzoic acid (AIT-082), as an exemplary potassium salt, tacrine hydrochloride (tetrahydroaminoacridine, THA, Sigma Chemical Co., St. Louis, Mo.), and physostigmine, hemisulfate salt (PHY, Sigma Chemical Co., St. Louis, Mo.). The drugs were dissolved in saline and prepared fresh daily. All injections were made at a volume of 0.1 ml/ 10 grams body weight. When testing drug effects, intraperitoneal (i.p.) injections of AIT-082 or THA were made one hour prior to the start of testing. Due to its shorter duration of action, PHY was injected 30 minutes prior to testing. Control subjects receive a similar injection of saline (vehicle).

To determine the duration of the memory trace, subjects were administered drug or saline and 30 minutes (PHY) or 1 hour (AIT-082 or THA) later they were given a single reference run with the milk reward in both goal boxes. After the indicated inter-trial delay, subjects were returned to the start box and given the first test trial with the milk reward only in the goal box opposite to the one entered on the previous correct trial. The subjects were given 10 trials with the reward alternating only after correct responses.

To determine if tolerance to the biological effects of AIT-082 developed, drug or saline was administered daily for 18 days prior to the testing in the standard win-shift paradigm.

Subjects were also trained in the same T-maze used for the win-shift model discussed above. As in the win-shift method, subjects were shaped and then given a single reference run in which reward was available in both goal boxes. The subject was only allowed to consume the milk reward in the goal box selected. On the next run, the reward and thus the correct response was in the same goal box selected for the reference run and was not alternated. The subject was required to learn that there was no shift in the goal box for the correct response. The subjects were given 10 trials per day and continued until the subject had at least 8 out of 10 correct responses on two consecutive days. The number of days to reach this criteria of performance was recorded. After the subject reached criteria, the goal box for the correct response was reversed. The number of days taken to reach criteria on reversal was recorded.

The results of the T-maze learning task and win-shift memory test are presented in Table J directly below.

TABLE J

Effect of AIT-082, THA and PHY at 90-Second Inter-trial Interval in Swiss Webster Mice

| Type of Test[1] | Control | THA | AIT-082 | | PHY |
|---|---|---|---|---|---|
| Dosage (mg/kg) | Saline | 1.25 | 0.5 | 30.0 | 0.125 |
| Win-shift Memory Test | | | | | |
| Correct responses (Correct respones/10 trials) | 4.6 | 7.1* | 6.5* | 8.2* | 6.5 |
| Latency time (seconds) | 2.68 | 8.22* | 1.95 | 2.03 | |
| Running time (seconds) | 1.95 | 3.65* | 2.20 | 1.95 | 2.65 |
| Locomotor Activity[2] | 343 | 671* | 323 | 378 | N/T |
| T-maze Learning (days to reach criteria | | | | | |
| Learning | 3.6 | N/T[3] | 3.0 | 3.3 | N/T |
| Reversal | 4.2 | N/T | 3.78 | 3.5 | N/T |
| Tolerance (Correct responses/10 trials) | 4.9 | N/T | N/T | 7.6* | N/T |

[1]at least 8 animals were run per group.
[2]Spontaneous movements per hour.
[3]Not tested.
*Indicates $p < 0.05$. Data analysis following significant ANOVA, a Dunnett test was run comparing drug tested groups with controls. An Arc Sign transformation was performed on percentage data and latencies were transformed to reciprocal time scores or speed scores.

As can be seen from the data in Table J, AIT-082 treatment resulted in an increased number of correct responses (memory) compared to saline control. While the effect was in the same range as with THA and PHY, both THA and PHY also increased latency time (prolonged the time to leave the start box, evidencing decreased motivation) and THA increased spontaneous locomotor activity. AIT-082 had no effect on learning or reversal and no tolerance developed to the memory enhancing effect of AIT-082 after 18 days of pre-treatment. Only AIT-082 enhanced memory function without affecting learning, motivation, performance and locomotor activity. Similar data have been observed with oral administration of AT-082.

EXAMPLE 19

Effect of AIT-082 Dosage on memory Trace Duration

Figure 7:
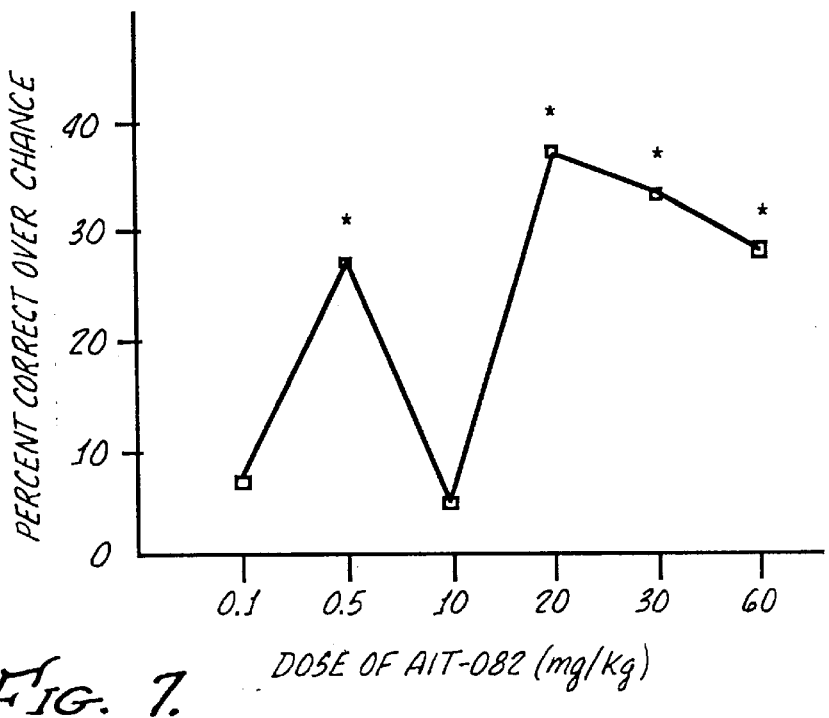
FIG. 7 is a graphical representation of the effects of different doses of the purine derivative AIT-082 on learning as measured in Swiss Webster mice using a win-shift memory test.
Figure 8:
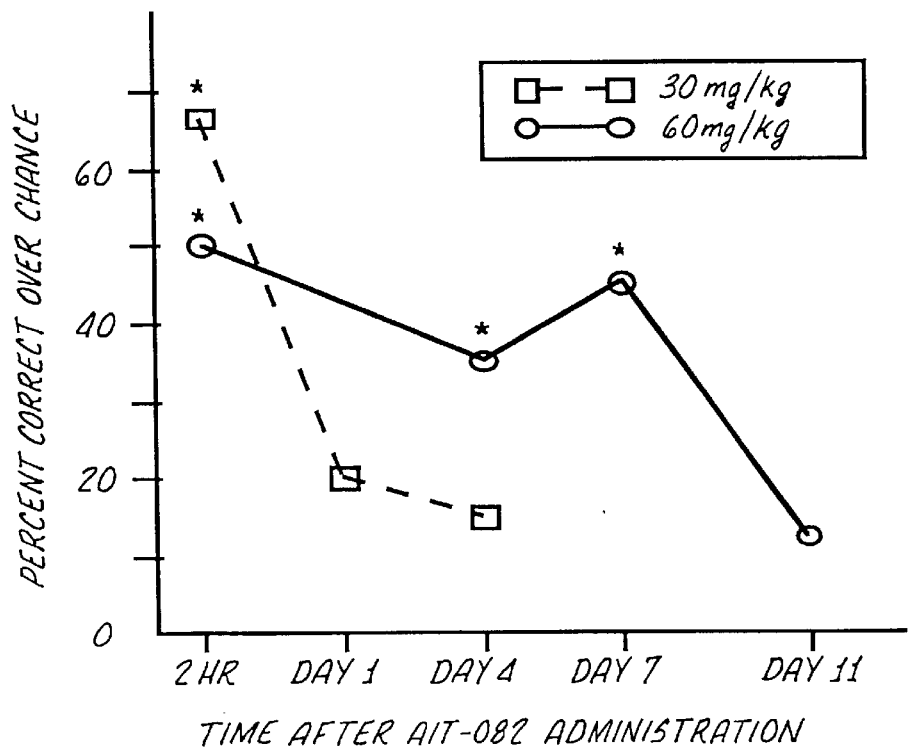
FIG. 8 is a graphical comparison of the duration of action of the purine derivative AIT-082 measured over time for single doses of 60 mg/kg and 30 mg/kg.

The dose response and duration of action of AIT-082 was studied in young adult Swiss Webster mice. The results are presented as the percent correct response over chance; chance being 50% correct. As shown in FIG. 7, AIT-082 is active in improving memory in normal adult Swiss Webster mice over a dose range from 0.5 to 60 mg/kg, with the optimal effect at 20 to 30 mg/kg. Further, as shown in FIG. 8, the onset of action is rapid (1 hour, data not shown) and lasts for more than seven days after a single dose of 60 mg/kg. Those skilled in the art will appreciate that the extended duration of the drug's effects will substantially lower the frequency of administration providing benefits in terms of patient compliance and cost.

EXAMPLE 20

Effect of AIT-082 on Memory Trace Duration in C57BL/6 Mice

Previous work has established that normal adult Swiss Webster mice have a memory trace duration of 60 seconds in the win-shift paradigm which may be increased by the administration of AIT-082. In order to further demonstrate the applicability and operability of the methods and compositions of the present invention, an alternative strain of mice having a different duration of memory trace was administered AIT-082, using the preceding protocol. The results are shown in Table K directly below.

TABLE K

Duration of Memory Trace in C57BL/6 Mice

| | Treatment Groups | | |
|---|---|---|---|
| | Control (Saline) | AIT-082 (30 mg/kg) | Physostigmine (0.125 mg/kg) |
| Inter-trial interval (sec) | No. above chance/Total# | Correctâ | No. above chance/Total# | Correct ◊ | No. above chance/Total# | Correctâ |
| 30 | 3/5 | 70 ± 11** | | | | |
| 60 | 3/5 | 70 ± 16** | | | | |
| 90 | 4/5 | 70 ± 6** | | | | |
| 120 | 4/5 | 78 ± 16** | | | | |
| 150 | 1/5 | 56 ± 10 | | | | |
| 180 | 2/7 | 58 ± 12 | 4/6 | 70 ± 15** | 3/6 | 65 ± 16* |
| 210 | | | 4/6 | 78 ± 15** | 1/6 | 53 ± 9 |

TABLE K-continued

Duration of Memory Trace in C57BL/6 Mice

| | Treatment Groups | | | | |
|---|---|---|---|---|---|
| | Control (Saline) | | AIT-082 (30 mg/kg) | | Physostigmine (0.125 mg/kg) | |
| Inter-trial interval (sec) | No. above chance/ Total[#] | Correct[a] | No. above chance/ Total[#] | Correct ◊ | No. above chance/ Total[#] | Correct[a] |
| 240 | | | 0/6 | 50 ± 6 | | |
| 270 | | | 0/6 | 50 ± 6 | | |

[#]No. subjects above chance (60% correct)/Total No. subjects tested
[a]/ = Mean score ± S.E.
**p < 0.01 (t-test against chance)
*p < 0.05 (t-test against chance)

Typically, in the win-shift foraging paradigm, C57BL/6 mice have a duration of memory trace of 120 seconds. As shown in Table K, at 30 mg/kg i.p., AIT-082 prolonged the duration of the memory trace to over 210 seconds. While physostigmine also prolonged the duration of the memory trace from 120 to 180 seconds in this model, it was not as active as AIT-082.

EXAMPLE 21

Treatment of Age Induced Memory Disorders Using AIT-082

In light of the preceding results, studies were performed to demonstrate that AIT-082 improves memory in mammals with neuronal disorders as well as in healthy subjects. Twelve-month old male Swiss Webster mice were screened for performance in the win-shift foraging test. Subjects were tested at various time delays, beginning at 10 seconds and increasing the inter-trial time interval to 30, 60, 90 and 120 seconds. The results for untreated mice are shown in Table L directly below.

TABLE L

Age-induced Working Memory Deficits in Swiss Webster Mice

| Duration of Memory Trace | No. of Subjects | % of Subjects | Degree of Memory Impairment |
|---|---|---|---|
| less than 10 seconds | 6 | 25 | Severe |
| 10 seconds | 8 | 33 | Moderate |
| 30 seconds | 10 | 42 | Mild |
| Total | 24 | 100 | |

The results in Table L demonstrate that individual subjects can be classified by the degree of working memory impairment. Subjects with severe impairment could not remember the correct response at 10 seconds while subjects with mild deficit could remember the correct response with a 30 second inter-trial interval but not at 60 seconds. Subjects with a moderate deficit could remember the correct response with a 10 second inter-trial interval but not at 30 seconds. Thus, the win-shift model can detect age-induced impairments in working memory. As will be appreciated by those skilled in the art, this observation is important since it provides the ability to use age-matched subjects with varying degrees of impairment for evaluation of potential therapeutic agents.

Following the establishment of a baseline, six subjects in each of the three groups were treated with AIT-082 (30 mg/kg, one hour before testing) or physostigmine (0.125 mg/kg, 30 minutes before testing) using the win-shift foraging test. The results are presented in Table M directly below and graphically represented in FIG. 9.

TABLE M

Effect of AIT-082 and PHY on the duration of memory trace in Swiss Webster mice with age-induced deficits

| Degree of Deficit | Inter-trial Interval (sec) | Control (Saline) | AIT-082 30 mg/kg | PHY 0.125 mg/kg |
|---|---|---|---|---|
| Mild | 60 | 0/6 | 6/6* | 5/6* |
| | 90 | | 4/6 | 3/6 |
| | 120 | | 2/6 | 2/6 |
| | 150 | | 1/6 | 2/6 |
| | 180 | | 1/6 | 1/6 |
| | 210 | | 0/6 | 0/6 |
| Moderate | 30 | 0/6 | 4/6* | 1/6 |
| | 60 | | 2/6 | 0/6 |
| | 90 | | 0/6 | |
| Severe | <10 | 0/6 | 0/6 | 0/6 |

Data is presented as the number of subjects performing significantly above chance/total number of subjects;
*Indicates p < 0.05 (t-test)

Six subjects had a severe deficit with no memory trace, they could not remember the task at 10 seconds. None of these subjects showed memory restoration with either AIT-082 or PHY treatment. In the six subjects with a moderate memory deficit who had a duration of memory trace of 10 seconds, AIT-082 increased the duration of the memory trace to greater than 30 seconds in 4 subjects (67% of the subjects) and increased the memory trace to greater than 60 seconds in two subjects (50%). In the six subjects with a mild memory deficit who had a duration of memory trace of 30 seconds, AIT-082 increased the duration of the memory trace in 2 subjects to 60 seconds, in 2 subjects to 90 seconds and in one subject each to 120 and 180 seconds. PHY increased the duration of the memory trace from 10 seconds to 30 seconds in only one animal in the moderate deficit group. In the mild deficit group, PHY increased the duration of the memory trace in 2 subjects to 60 seconds, in one subject to 90 seconds and in two subjects to at least 180 seconds. Thus, AIT-082 is more active than physostigmine in the moderate deficit group and at least as active in the mild deficit group.

EXAMPLE 22

Treatment of Age Deficit Memory Disorder Using AIT-082

Twelve-month old male C57BL/6 mice were screened for performance in the win-shift foraging test. Subjects were tested at various inter-trial time intervals. Subjects who could not perform to criteria (>60% correct) at 10 seconds delay were classified as having a severe deficit. Subjects who performed to criteria at 10 seconds but not at 30 seconds were classified as having a moderate degree of deficit and subjects who performed to criteria at 30 seconds but not at 60 seconds were classified as having mild deficit. As in Example 21, subjects in each group were treated with either AIT-082 or PHY to determine the extent to which the working memory trace was prolonged. The results are presented in Table N directly below and graphically represented in FIG. 10.

TABLE N

Effect of AIT-082 and PHY on the duration of memory trace in C57BL/6 mice with age-induced deficits

| Degree of Deficit | Inter-trial Interval (sec) | Control (Saline) | AIT-082 30 mg/kg | PHY 0.125 mg/kg |
|---|---|---|---|---|
| Mild | 60 | 0/6 | 4/4* | 7/8* |
|  | 90 |  | 2/4* | 3/8 |
|  | 120 |  |  | 2/8 |
|  | 150 |  |  | 2/8 |
|  | 180 |  |  | 2/8 |
|  | 210 |  |  | 0/8 |
| Moderate | 10 | 6/6 | 6/6* | 6/6 |
|  | 30 | 0/6 | 4/6 | 1/6 |
|  | 60 |  | 1/6 | 0/6 |
|  | 90 |  | 0/6 |  |
| Severe | <10 | 0/6 | 0/6 | 0/6 |

Data is presented as the number of subjects performing significantly above chance/total number of subjects;
*Indicates $p < 0.05$ (t-test)

In the mild deficit group, AIT-082 prolonged the duration of the memory trace from 30 to 90 seconds, and from 10 to 30 seconds in the moderate deficit group. While PHY prolonged memory in the mild group, it was ineffective in the moderate group. Therefore AIT-082 restored working memory deficits in both normal mice and mice with age induced neuronal disorder for both Swiss Webster and C57BL/6 strains. Specifically, the results show that AIT-082 restores working memory in mice with mild and moderate memory deficits. Based on the other Examples previously provided it is reasonable to conclude that it accomplishes this restoration by modifying the carbon monoxide dependent guanylyl cyclase system.

EXAMPLE 23

Prophylaxis of Age Deficit Memory Disorders Using AIT-082

Figure 11:
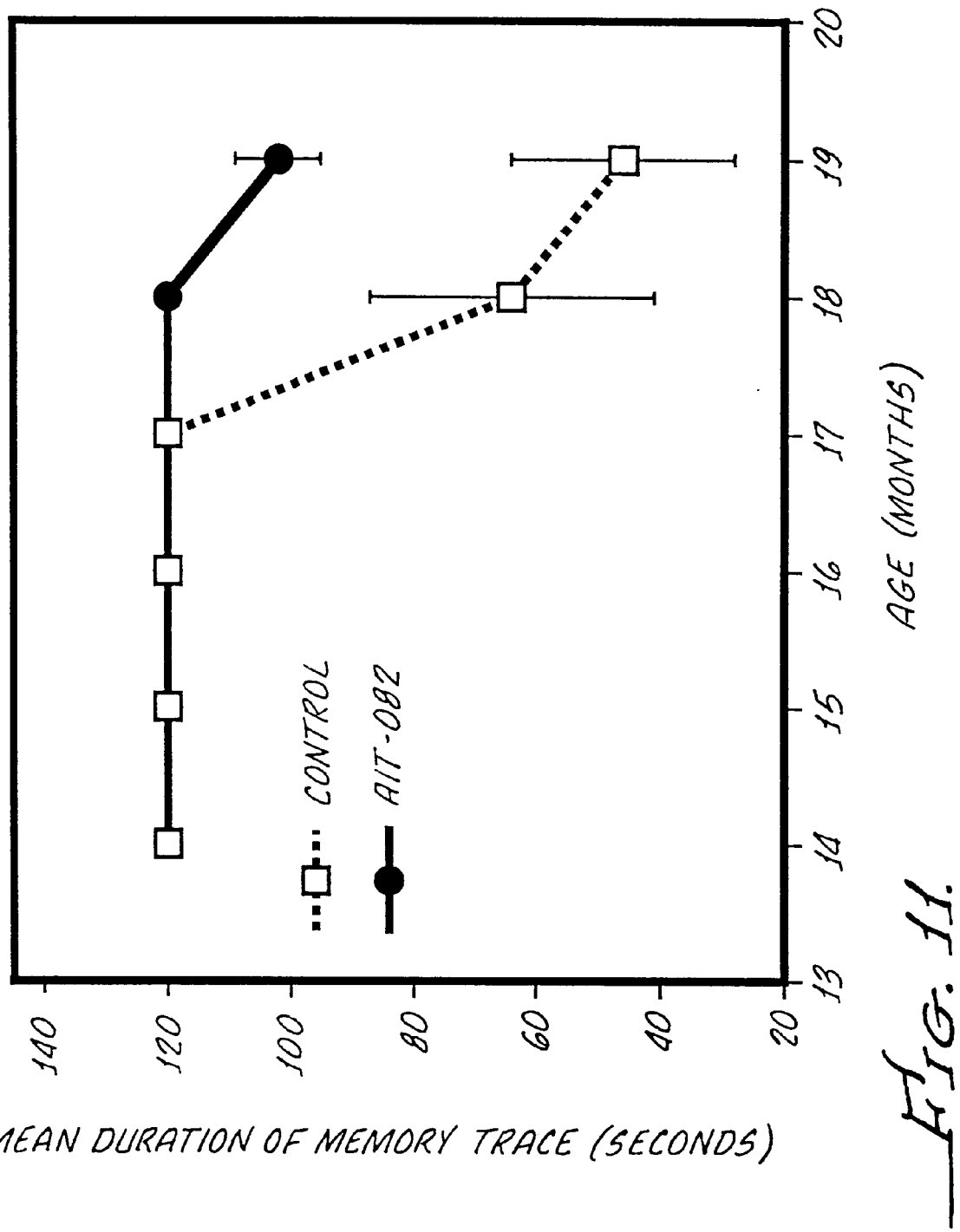
FIG. 11 is a graphical comparison of age-induced memory deficit prophylaxis in mice treated with the purine derivative AIT-082 and untreated mice.

It has been observed that age-induced memory deficits typically begin to manifest themselves in mice between 14 and 16 months of age. Therefore, we began treating mice at 14 months of age with AIT-082 (30 mg/kg/day) in their drinking water. The animals were measured monthly for their memory using the win-shift foraging tests previously described. The results are shown in FIG. 11 and show that the administration of AIT-082 delayed the onset and severity of memory deficits

EXAMPLE 24

Prophylaxis of Alcohol-Induced Deficit Memory Disorders Using AIT-82

In order to demonstrate the broad applicability of the methods of the present invention with respect to different types of neurodegenerative disorders, AIT-082 was used to retard the production of alcohol induced memory deficit. Six month old male C57BL/6 mice were evaluated in the win-shift model in combination with treatment with ethanol, a non-specific memory suppressant, and AIT-082. Subjects were treated with saline (control) or AIT-082 (30 mg/kg. i.p.) 1 hour prior to testing. Ethanol was administered at a dose of 0.5 gm/kg i.p. ten minutes prior to testing. The results of a pilot study are presented in Table O directly below.

TABLE O

Working memory deficit produced by ethanol and its reversal by AIT-082

| | Treatment | | |
|---|---|---|---|
| | Control | Ethanol | Ethanol + AIT-082 |
| Correct trials[1,2] | 8.08 ± 0.29 | 6.5 ± 26* | 7.89 ± 0.54[†] |
| Latency time (sec)[2] | 1.24 ± 0.17 | 1.18 ± 0.10 | 1.77 ± 0.27 |
| Running time (sec)[2] | 1.44 ± 0.35 | 1.17 ± 0.08 | 3.22 ± 0.61*[†] |
| Number of subjects | 13 | 13 | 9 |

[1]Indicates mean number of correct responses per 10 trials;
[2]Indicates mean value ± S.E.;
*Indicates $p < 0.05$ (t-test) compared to control;
[†]Indicates $p < 0.05$ (t-test) compared to ethanol.

The results in Table O demonstrate that it is possible to identify a dose of a blocking agent that can produce a memory deficit as measured in the win-shift model. Ethanol was selected as a non-specific blocking agent and its effects were reversed by administration of AIT-082 prior to the treatment with ethanol. Therefore it would appear feasible to evaluate other more specific blocking agents which have activity at specific receptor sites.

In addition to AIT-082 other purine derivatives are believed to play a role in neuronal survival, synaptogenesis and recovery of function following injury or cell death in the central nervous system. For example, similarities between guanosine and AIT-082 indicate that AIT-082 and guanosine act through comparable mechanisms. That is, both appear to act as carbon monoxide dependent guanylyl cyclase modulators. Further, it is known that after cells are damaged, they leak massive amounts of both purine nucleosides and nucleotides to the extracellular space. The extracellular concentration of guanosine in the region of a focal brain injury may reach 50 mM and is elevated up to five fold for at least seven days. Therefore, following injury, astrocytes or glia and neurons are exposed to high extracellular concentrations of guanosine.

Accordingly, the following studies were undertaken in order to demonstrate the effectiveness of using other exemplary purine derivatives such as guanosine to modulate the carbon monoxide dependent guanylyl cyclase system.

EXAMPLE 25

Astrocytes Produce Tropic Factors Upon Exposure to Guanosine and GTP

Astrocytes appear to proliferate in response to extracellular guanosine or guanosine triphosphate (GTP). GTP or guanosine may also stimulate the release of trophic factors from cultures of neocortical astrocytes from neonatal mouse brains. Astrocytes were incubated with different concentrations of guanosine of GTP respectively. Neurotrophin immunoreactivity in the culture medium from treated cells was then measured by ELISA.

Briefly, 96 well Falcon plates (Fisher) were coated with 1 mg/ml of sheep mono-specific anti-NGF IgG (affinity column purified) contained in 0.1M sodium carbonate buffer pH 9.6. After an overnight incubation at 4° C. blocking solution (PBS with 10% goat serum) was added to remove excess antibody. After a four hour incubation at room temperature the plates were washed 3 with PBS containing 0.05% Tween 20. The conditioned media and standard 2.5S HPLC purified NGF were added and incubated overnight. The next day plates were washed 3 times with PBS-0.05% Tween 20. The secondary antibody, rabbit mono-specific anti-NGF IgG conjugated with b-galactosidase (Pierce-SPDP method) (1:500 dilution) was added. The plates were incubated overnight at 4° C. The next day the plates were washed 3 times with PBS-0.05% Tween 20. To each, well substrate, 0.2 mM 4-methylumbelliferyl-b-galactoside (MUG) in 0.1M phosphate buffer (1 mMM MgCl2 pH 7.2) was added. After a 4 hour incubation at room temperature the reaction was stopped by the addition of 0.1M glycine, pH 10.3. Samples were then read using Microfluor ELISA reader (excitation 360 nm; emission 450 nm). The sensitivity of this assay was 10 pg/well NGF.

Figure 12A:
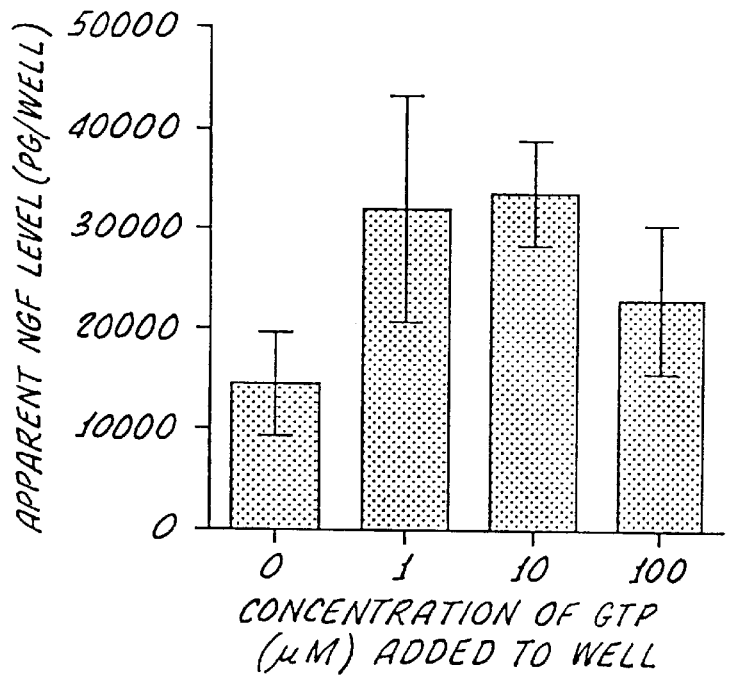
FIGS. 12A and 12B are graphical comparisons of the production of nerve growth factor by murine cortical astrocytes in response to the addition of purine derivatives as measured using an ELISA assay.
Figure 12B:
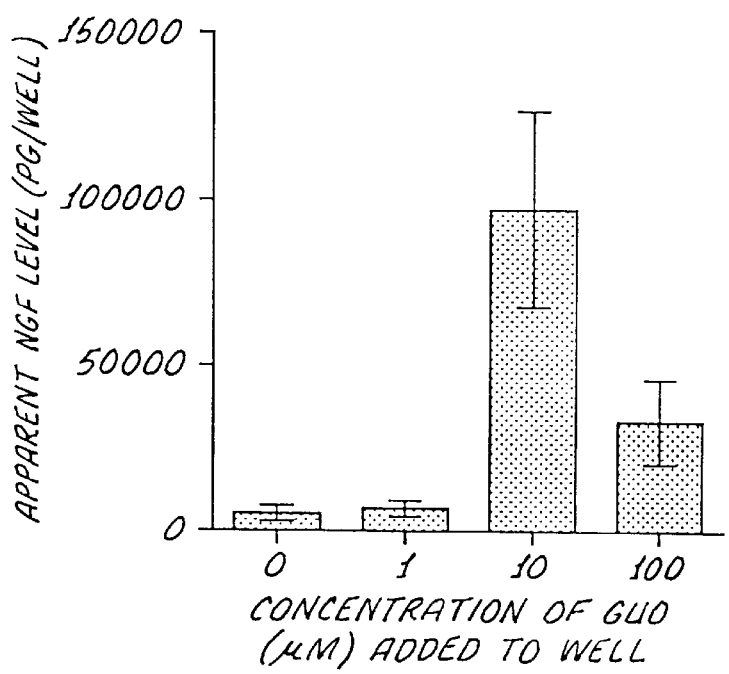

The ELISA assay detected neurotrophins NGF and NT-3 with almost equal affinity and BDNF with 100 times less affinity. As shown in FIGS. 12A and 12B, both guanosine and GTP increased the amount of NGF-like immunoreactivity in the culture medium. The astrocytes exposed to the various levels of guanosine produced a much stronger response than those exposed to equivalent concentrations of GTP.

EXAMPLE 26

Astrocytes Produce Neutothopics Factors Upon Exposure to Guanosine

Figure 13A:
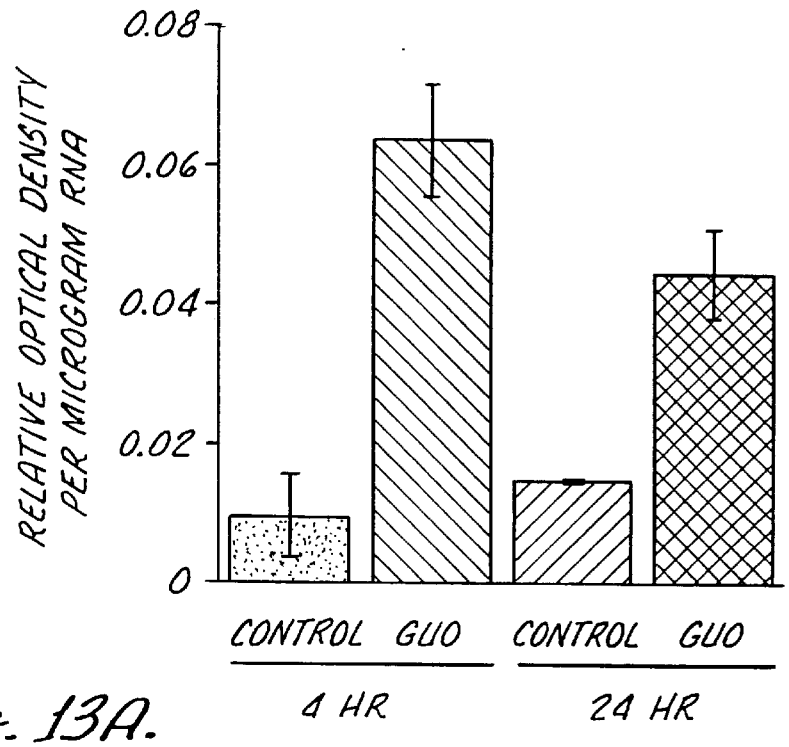
FIGS. 13A and 13B are graphical comparisons of the production of various neurotrophic factor mRNA by murine cortical astrocyte cells grown in the presence and absence of guanosine at different times.
Figure 13B:
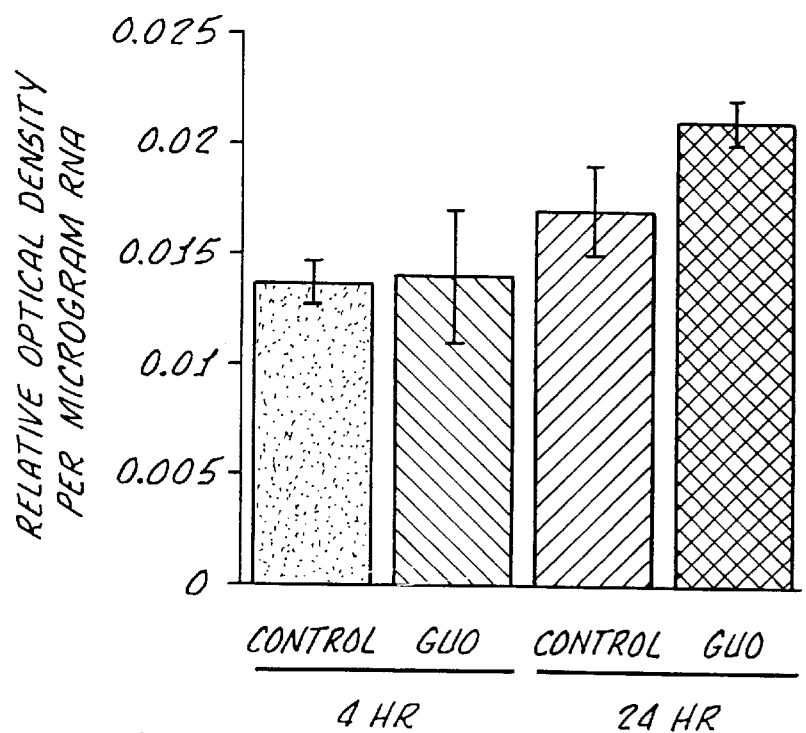

In order to confirm the results of the previous assay, mRNA levels of the tropic factors FGF-2 and NGF were measured in astrocytes which had been exposed to guanosine. The mRNA levels were measured using the same protocol used previously in Example 16. As shown in FIGS. 13A and 13B, the addition of guanosine increased NGF and FGF-2 mRNA at 4 hours and at 24 hours, respectively, after it was added to astrocytes. The observed increase in neurotrophin mRNA is important following brain injury or recovery from brain injury when the extracellular concentration of guanosine is considerably high. As cells are exposed to a high concentration of guanosine for several days following brain injury, this data indicates that guanosine may be responsible for some of the recovery of function.

As previously discussed, an agent that can penetrate the blood brain barrier and increase concentrations of neurotrophic factors as measured here by mRNA levels should have a substantial positive effect on neuronal survival and on the formation of collateral nerve circuits. In turn, this should enhance functional recovery in many different neurological diseases or after damage to the nervous system.

EXAMPLE 27

Neurons Undergo Neuritogenesis Upon Exposure to Guanosine

Figure 14A:
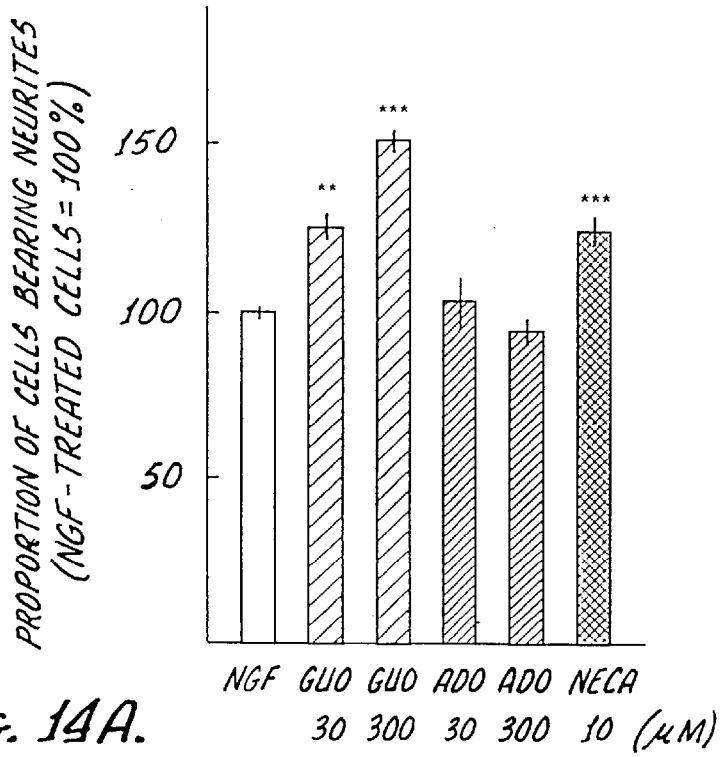
FIGS. 14A, 14B and 14C are graphical comparisons of neurotogenic responses to different concentrations of purine derivative in the presence and absence of nerve growth factor.
Figure 14B:
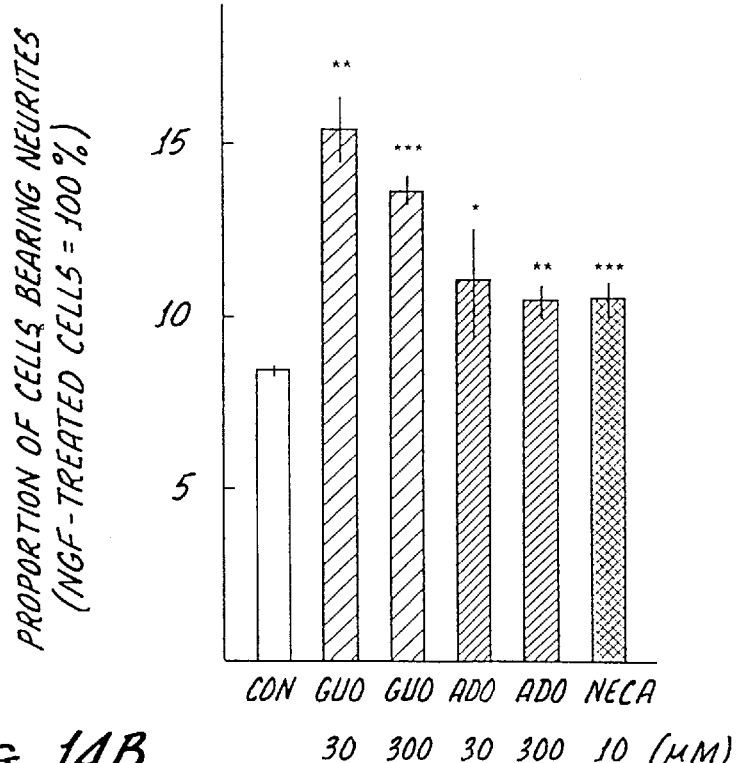

In addition to changes in glia or astrocytes, important neuronal changes also take place following focal brain injury. Neuritic processes of surviving neurons may undergo neuritogenesis. Accordingly, based on previous results using AIT-082, studies were performed to demonstrate that guanosine may also modify carbon monoxide guanylyl cyclase to stimulate neuritogenesis. As previously discussed, because PC12 cells constitute a homogeneous population of neuronal-like cells, without contaminating astroglia-type cells, the direct effects of the exemplary purine derivatives of the present invention on neurite outgrowth in these cells can be observed easily. Accordingly, PC12 cells were exposed to guanosine and adenosine with and without NGF and monitored as in Example 12. The effects of exposure to purine derivatives with NGF are shown in FIG. 14A while exposure without NGF is shown in FIG. 14B. A direct comparison of the effects of these purine derivatives with and without the presence of NGF is shown for each compound in FIG. 14C.

As shown in FIG. 14A, guanosine, but not adenosine, enhanced the neurite outgrowth induced by NGF in PC12 cells after 48 hours. The enhancement was significant over that of NGF alone at guanosine concentrations of 30 and 300 mM. Adenosine did not enhance NGF induced neurite outgrowth at any concentration. This indicates that neurite outgrowth induced by purines is not just a generalized phenomenon. 5'-N-ethylcarboxamidoadenosine (NECA), an adenosine $A_1$ and $A_2$ receptor agonist, also enhanced neuritogenesis, but not to the same extent as guanosine.

On their own, in the absence of NGF, both adenosine and guanosine slightly increased the proportion of cells with neurites as shown in FIG. 14B. The effects of guanosine at both 30 and 300 mM was greater than adenosine at the same concentrations. In the presence of (NECA), there was little stimulation of neurite outgrowth. Because the effects of the compounds in the presence of NGF were much more readily scored and less variable from experiment to experiment than with the compounds alone, most of the data for enhancement of neurite outgrowth was determined in the presence of NGF.

Figure 14C:
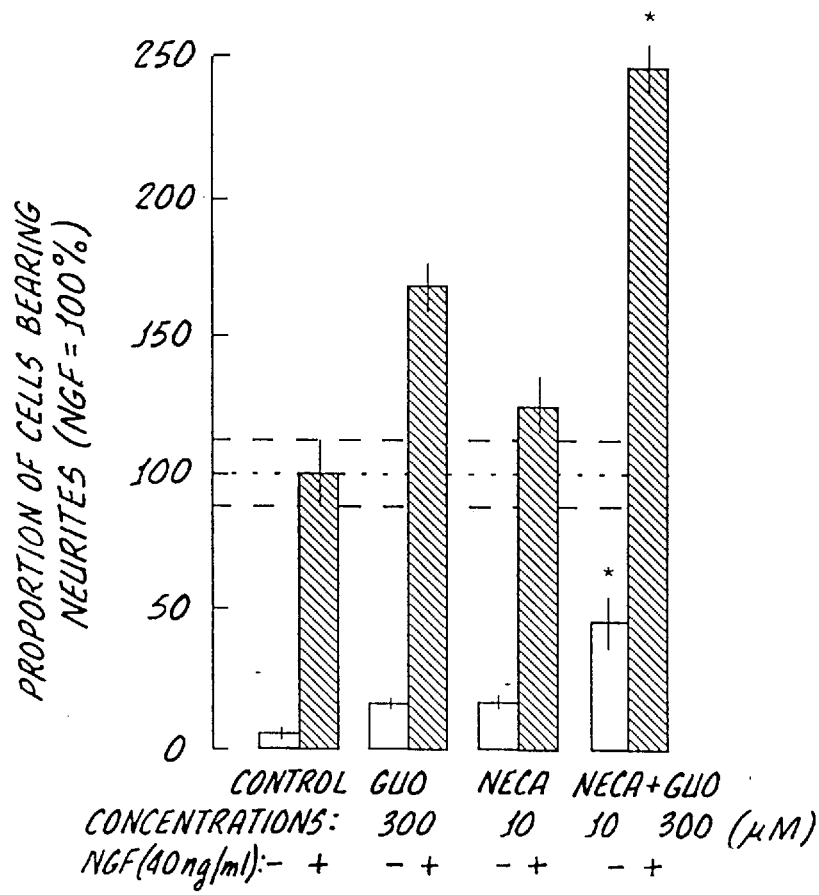

The comparative data shown in FIGS. 14A and 14B and emphasized in FIG. 14C show that guanosine causes some neurite extension, but can also react synergistically to enhance the trophic effects of NGF. Adenosine, although slightly enhancing neurite outgrowth on its own does not enhance the effects of NGF. Interestingly, NECA but not adenosine could synergistically enhance the actions of guanosine, both in the presence and absence of NGF as shown in FIG. 14C. The fact that adenosine did not increase NGF-dependent neurite outgrowth in PC12 cells but that guanosine did, suggests that they interact differently with PC12 cells. Adenosine would interact with adenosine receptors, such as the A2 purinoceptor. This would activate adenylate cyclase which increases intracellular cAMP. NECA apparently acts in this manner. But the effects of NECA were synergistic with those of guanosine. This indicates that guanosine and NECA use different signalling pathways to enhance neurite outgrowth.

EXAMPLE 28

Various Purine Derivatives Provide Different Rate of Neuritogenesis

In view of the previous results, other exemplary purine derivatives were examined to demonstrate the specificity of those compounds which modulate carbon monoxide dependent guanylyl cyclase to modify neural activity. Specifically, different concentrations of the purine derivatives inosine, hypoxanthine and xanthine were tested in the presence of NGF using the protocol of Example 12 to demonstrate their ability to modify neural activity.

Figure 15A:
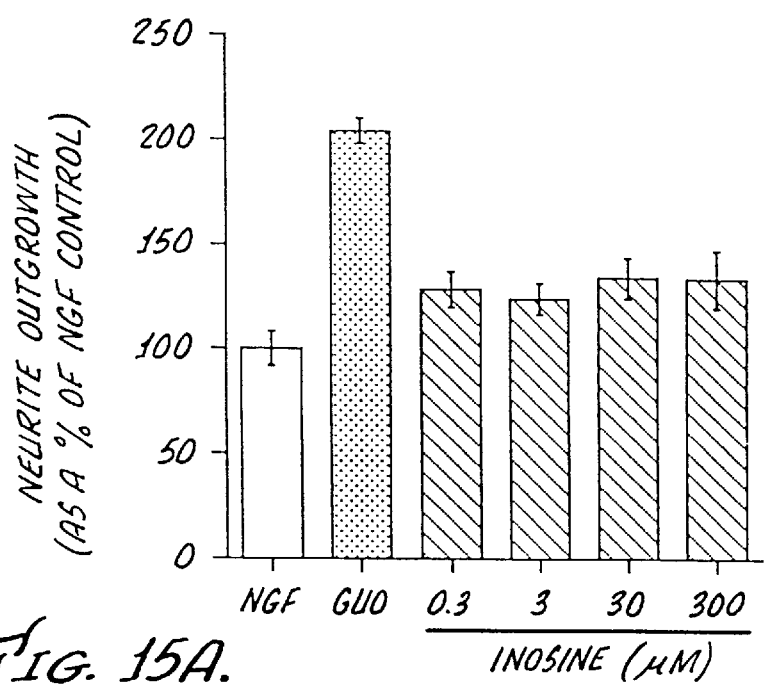
FIGS. 15A, 15B and 15C are graphical comparisons of nerve growth factor mediated neurotogenic responses in neurons grown in the presence of various concentrations of different purine derivatives.

As shown in FIG. 15A, inosine only slightly enhanced neurite outgrowth over that produced in cells treated with NGF alone. This was true for concentrations of inosine ranging from 0.3 to 300 mM. FIG. 15A also shows that the action of inosine on the enhancement of neurite outgrowth was much less effective than that of guanosine.

Figure 15B:
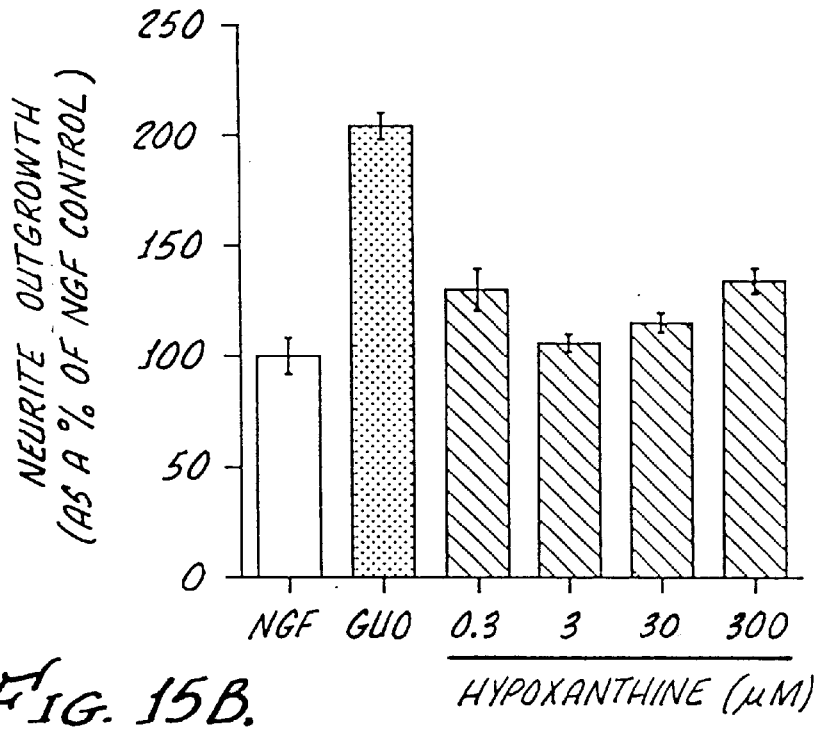
Figure 15C:
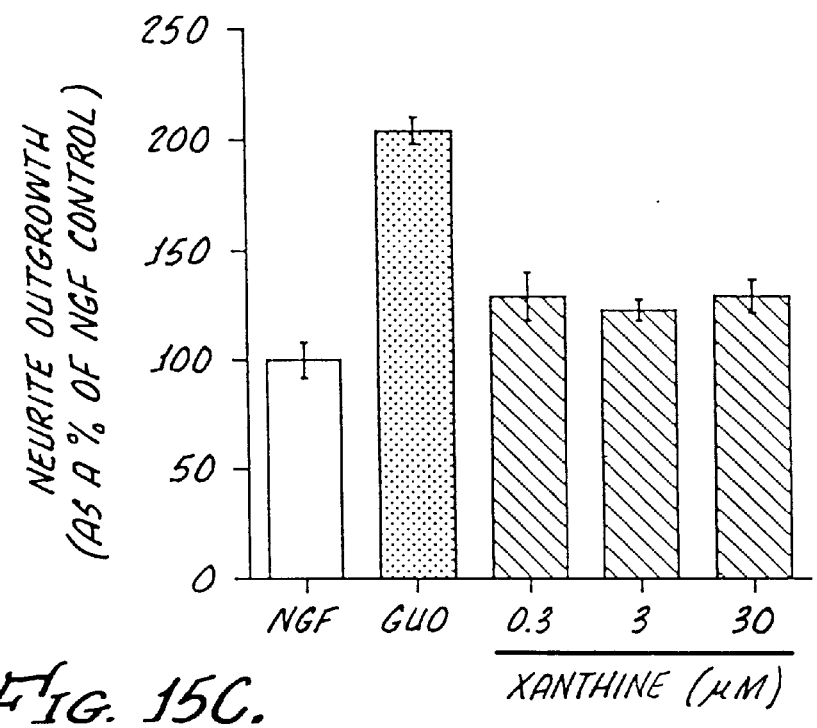

FIGS. 15B and 15C also show that hypoxanthine and xanthine each produced results similar to that of inosine on NGF-induced neuritogenesis. In FIG. 15C xanthine, in concentrations from 0.3 to 30 mM (300 mM was toxic to the cells), only slightly enhanced NGF-induced neurite outgrowth. FIG. 15B shows that hypoxanthine showed the greatest, although still modest, enhancement at concentrations of 0.3 and 300 mM, although other concentrations had no significant enhancement. Even though some enhancement of neurite outgrowth was observed with hypoxanthine, the relative amount of enhancement was not nearly as great as was the effect of guanosine. These results indicate that inosine, xanthine and hypoxanthine do not modulate the carbon monoxide-dependent guanylyl cyclase system to modify neural activity but rather influence other signaling mechanisms.

EXAMPLE 29

Effects of AIT-34 on Neuritogenesis

Figure 16:
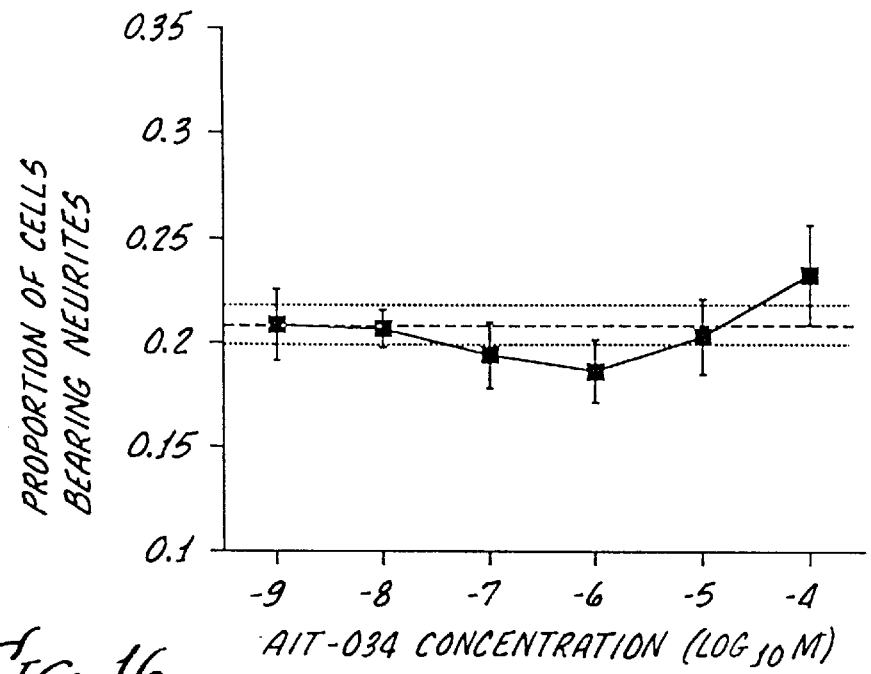
FIG. 16 is a graphical representation of nerve growth factor mediated neuritogenesis measured for neuronal cells grown at various concentrations of the purine derivative AIT-034.

To demonstrate the effects of compounds similar to AIT-082 on neuritogenesis, PC12 cells were exposed to AIT-34, otherwise known as 3(1,6 dihydro-6-oxo-9 h purin-9-yl)-N-(3-(2-oxopyrrolidin-1-yl) propyl) propanamide, during growth and monitored according to Example 12. As shown in FIG. 16, different concentrations of AIT-034 did not enhance NGF-induced neuritogenesis as is observed with AIT-082.

EXAMPLE 30

Effects of ATP and GTP on Neuritogenesis

To further demonstrate that purine derivatives having different functional groups may be used in accordance with the teachings of the present invention, PC12 cells were exposed to adenosine triphosphate (ATP) and guanosine triphosphate (GTP) and monitored for neuritogenesis using the protocol of Example 12.

Figure 17:
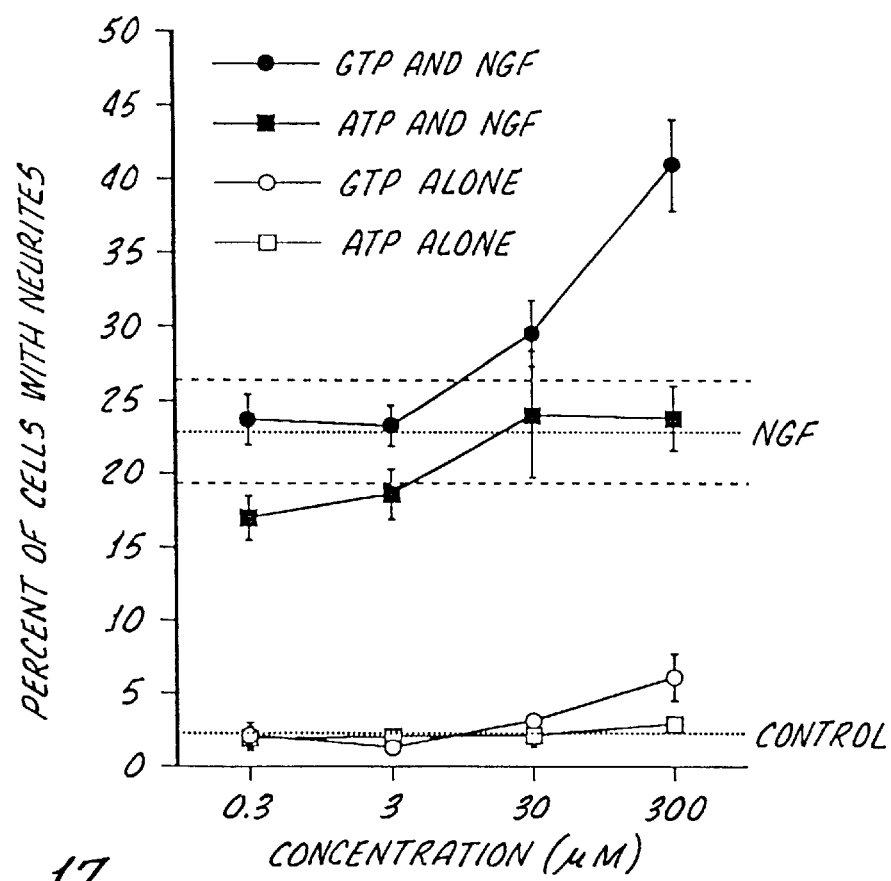
FIG. 17 is a graphical comparison of neurotogenic response of neuronal cells grown at various concentrations of guanosine triphosphate and adenosine triphosphate with and without nerve growth factor.

In a manner very similar to the actions of adenosine and guanosine on neurite outgrowth in PC12 cells, their corresponding nucleotides ATP and GTP had parallel effects on neurite outgrowth. As shown in FIG. 17, ATP did not enhance neuritogenesis in either NGF treated cells or on its own. In sharp contrast, GTP at 30 and 300 mM, did enhance neuritogenesis in the presence of NGF and further elicited neurite outgrowth on its own.

Figure 18:
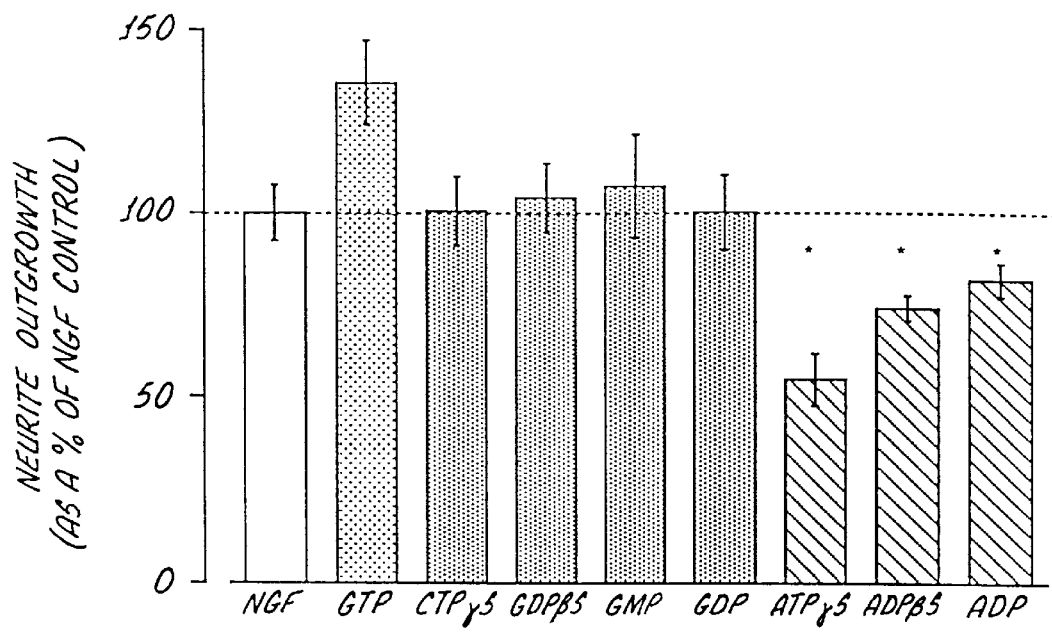
FIG. 18 is a graphical comparison of nerve growth factor mediated neurotogenic response to monophosphate, diphosphate, and triphosphate purine derivatives of guanosine and adenosine.

However, as shown in FIG. 18, GTP did not appear to be acting as a source from which guanosine was released in a controlled manner. If GTP was hydrolyzed to guanosine diphosphate (GDP), guanosine monophosphate (GMP) and finally to guanosine by ectoenzymes, one would predict that GDP and GMP would also enhance neurite outgrowth from PC12 cells. Yet, neither GDP nor GMP were effective alone or with NGF in eliciting neurite outgrowth. By way of comparison, the adenine-based compounds all had an inhibitory effect.

EXAMPLE 31

Guanosine but Not GTP Increases cGMP in PC12 Cells

Figure 19:
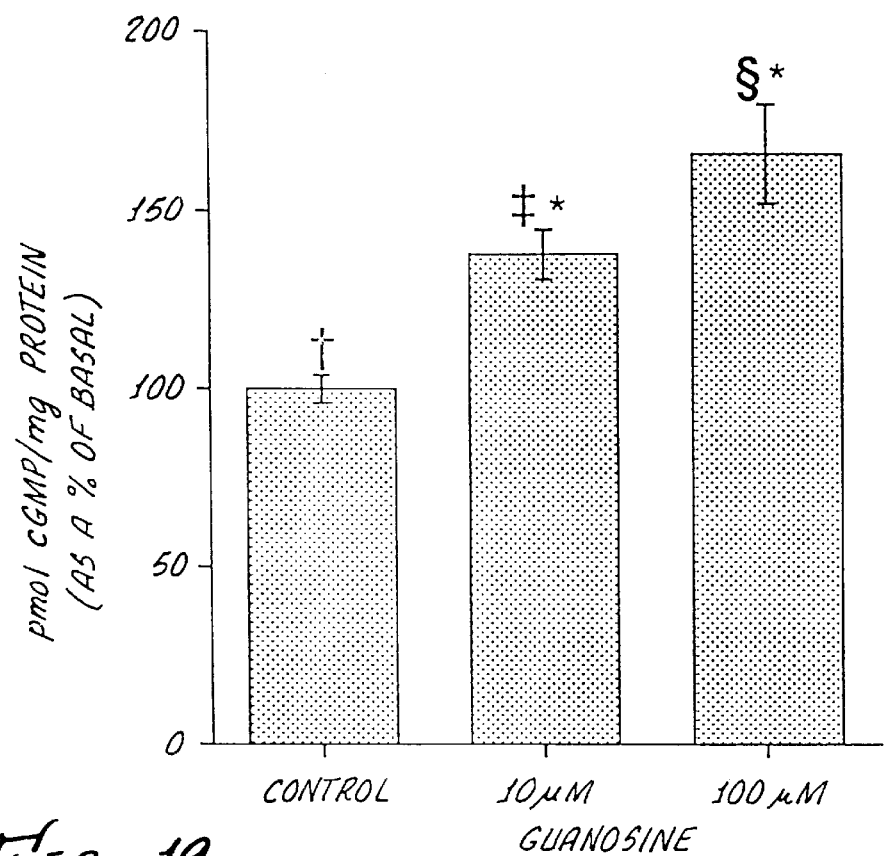
FIG. 19 is a graphical comparison of cyclic GMP produced in neuronal cells grown in the presence of different concentrations of the purine derivative guanosine.

Based on the previous examples, a study was conducted to demonstrate the neurotogenic mechanisms of GTP and guanosine respectively. Guanosine and GTP have been shown to increase intracellular cyclic 3',5'-guanosine monophosphate (cGMP) in arterial smooth muscle. Since cGMP analogues have been reported to stimulate neurite outgrowth from neuroblastoma cells it was possible that both guanosine and GTP might exert their effects through increasing intracellular cGMP. As shown in FIG. 19, guanosine increased intracellular cGMP in PC12 cells as determined by radio-immunoassay using the protocol detailed in Example 15. Such an increase would be expected of a carbon monoxide dependent guanylyl cyclase modulator. In contrast, it was found that GTP did not increase levels of cGMP, indicating that any GTP-stimulated neuritogenesis occurs by another mechanism.

EXAMPLE 32

Use of Non-Selective Inhibitors of Guanylyl Cyclase Reduces Guanosine Neuritogenesis To demonstrate that guanosine modifies the carbon monoxide-dependent guanylyl cyclase system, studies were conducted to show that increased levels of intracellular cGMP were necessary for guanosine to enhance NGF's neurotogenic effects on PC12 cells. In particular, different concentrations of three inhibitors of guanylyl cyclase were added to PC12 cells with guanosine. Neuritogenesis was then determined using the protocol of Example 12.

Figure 20A:
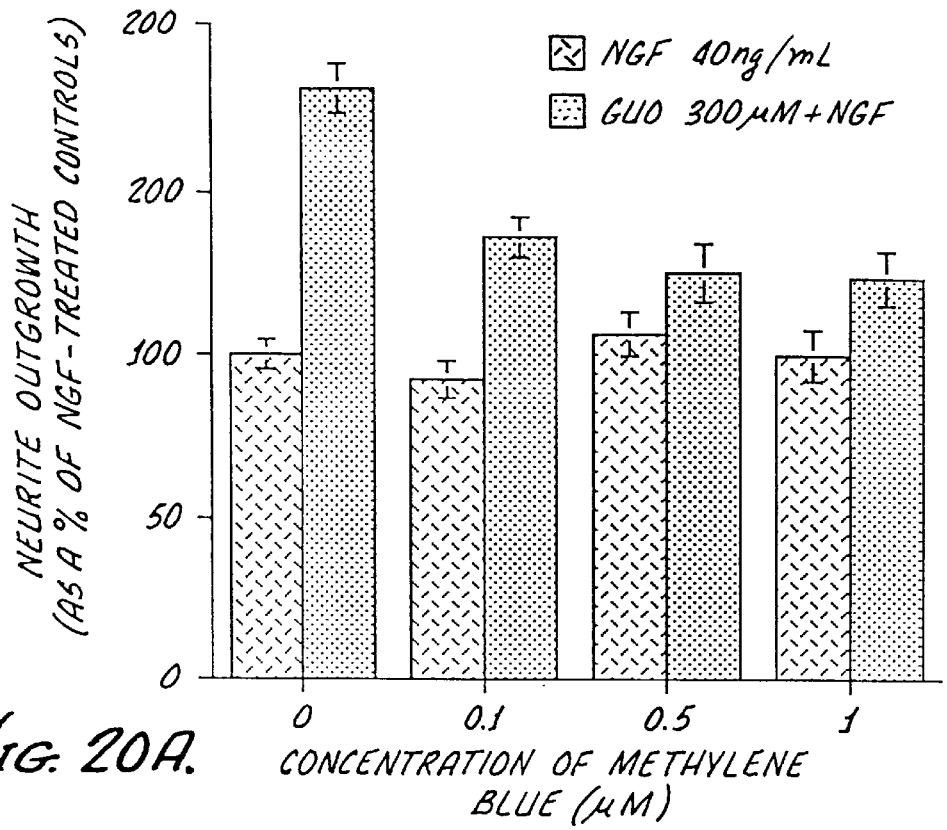
FIGS. 20A, 20B and 20C are graphical comparisons of nerve growth factor mediated neurotogenic responses of cells grown with and without the purine derivative guanosine in the presence of various concentrations of three different inhibitors.

Methylene Blue (MB) inhibits soluble guanylyl cyclase (sGC), the enzyme that synthesizes cGMP. As shown in FIG. 20A the addition of MB (0.1–5 mM) to cultures of PC12 cells abolished the synergistic effects of guanosine with NGF. Conversely, MB had no effect on NGF-stimulated neurite outgrowth.

Figure 20B:
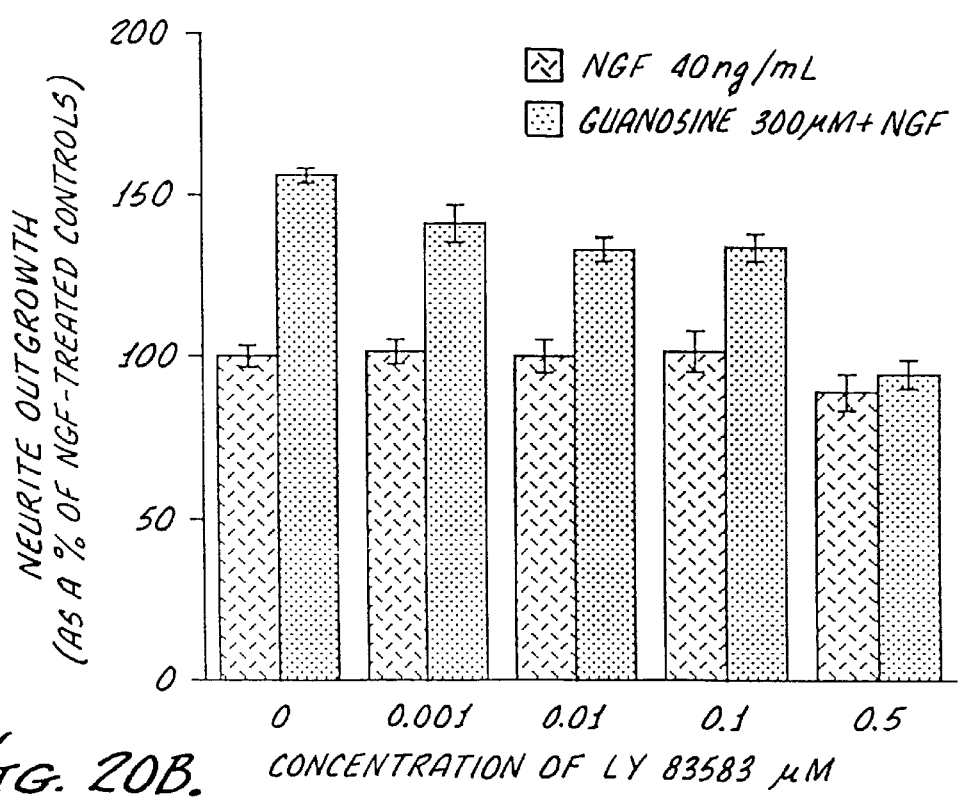

LY83583 inhibits both particulate and sGC. FIG. 20B shows that the neurite outgrowth response elicited by guanosine was inhibited by LY83583, but the response elicited by NGF was unaffected. The mechanism by which LY83583 inhibits guanylyl cyclase is unresolved, but is likely indirect, involving glutathione metabolism. Therefore, two non-selective inhibitors of guanylyl cyclase, each with a different mechanism of action, attenuated the neurotogenic action of guanosine.

These data indicate that guanosine and NGF act through different mechanisms. They also indicate that increases in intracellular cGMP were necessary, although possibly not sufficient, for guanosine to exert its neurotogenic effects.

Figure 20C:
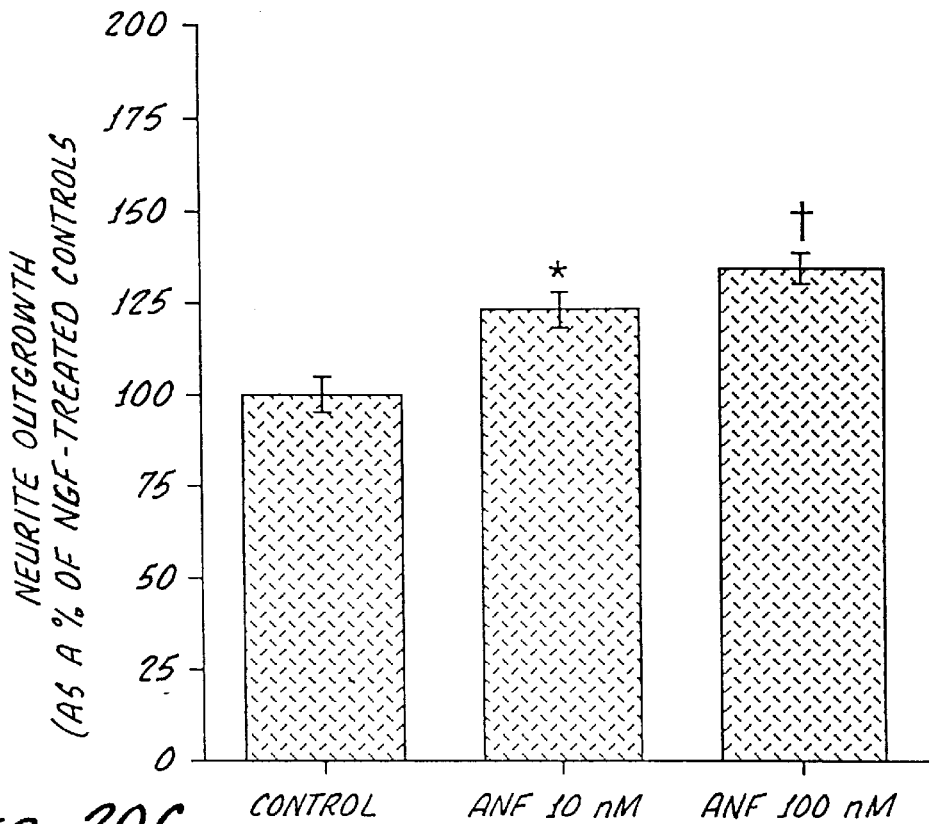

To test whether increases in cGMP were sufficient to cause neurite outgrowth, atrial natriuretic factor (ANF) was added to cell cultures in a manner similar to that used for guanosine. ANF is a hormone whose only known signal transduction pathway is through activation of particulate guanylyl cyclase. As shown in FIG. 20C, ANF, like guanosine, enhanced NGF-stimulated neurite outgrowth from PC12 cells indicating that increased intracellular cGMP production, induced by carbon monoxide dependent guanylyl cyclase or other mechanisms assisted in stimulating neurite outgrowth.

EXAMPLE 33

Nitric Oxide or Carbon Monoxide Promotes Guanosine Neuritogenesis

Since guanosine increased intracellular cGMP as shown in Example 31, studies were performed to demonstrate whether its signal could be transduced through production of NO or CO. If NO was involved, then addition of nitric oxide donors that liberate NO should mimic the effects of guanosine.

Figure 21:
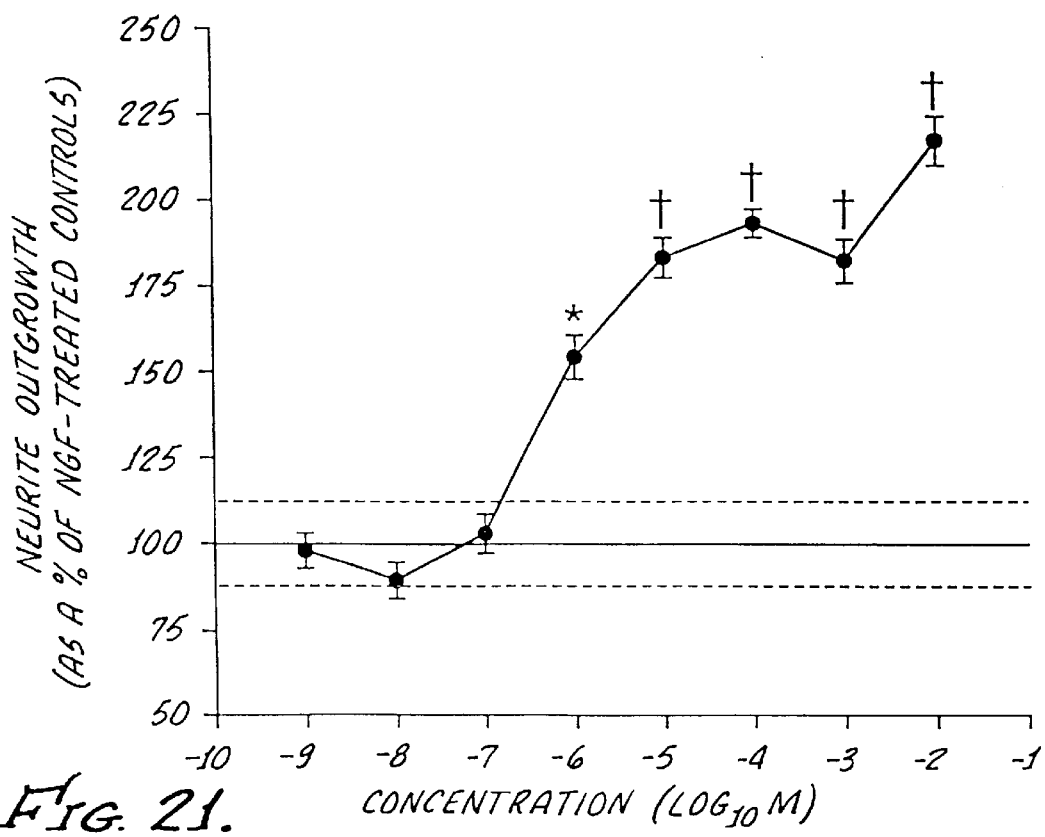
FIG. 21 is a graphical representation of nerve growth factor-mediated neurotogenic responses for neurons grown in the presence of sodium nitrate, an inorganic nitric oxide donor.
Figure 22A:
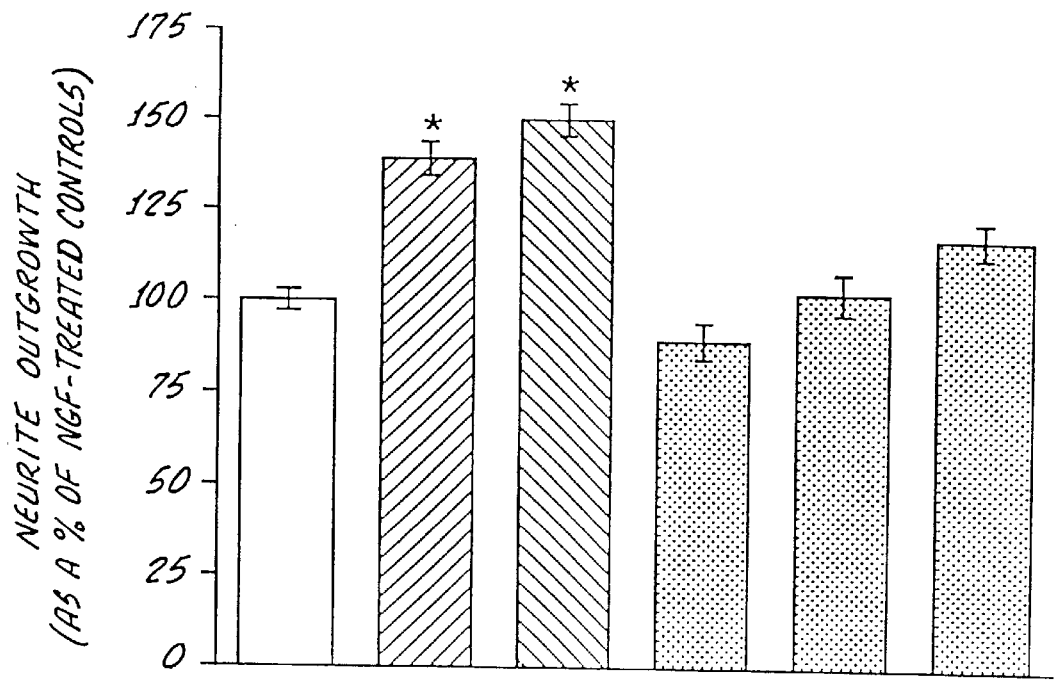
FIGS. 22A and 22B are graphical comparisons of nerve growth factor mediated neurotogenic response of neurons grown in the presence of nitric oxide donors and scavengers of nitric oxide and carbon monoxide.
Figure 22B:
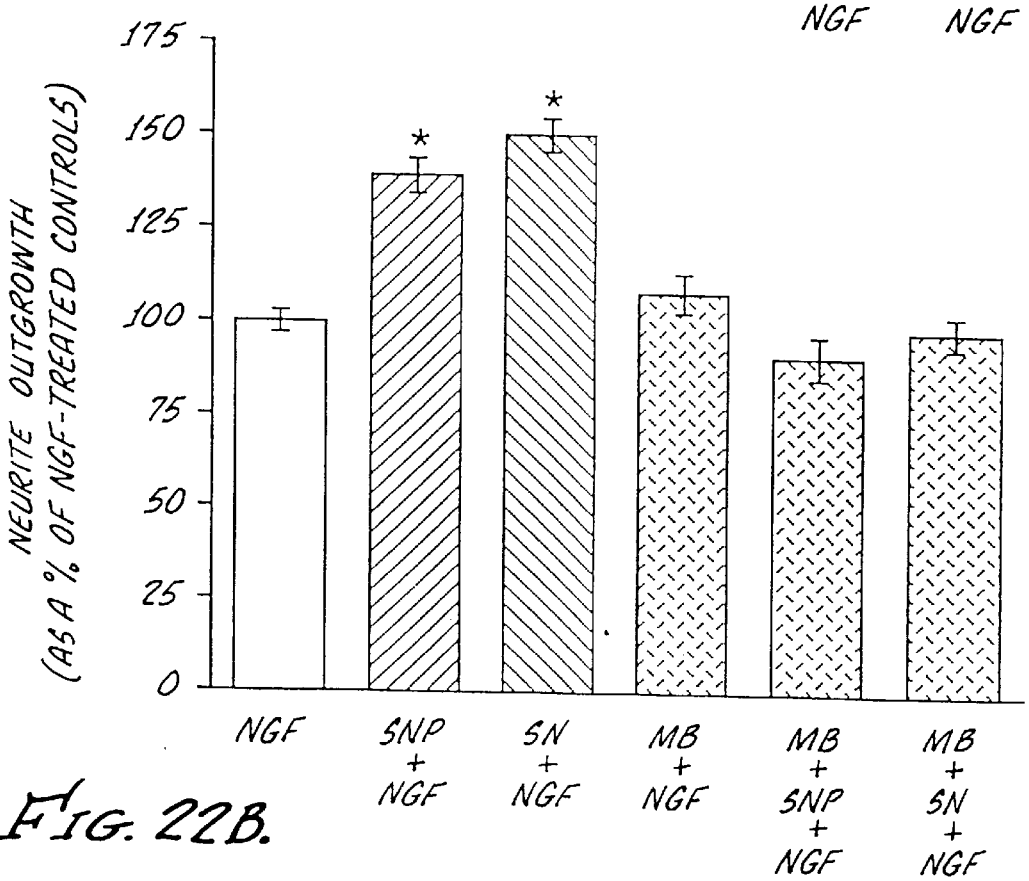

PC12 cells were grown for 48 hours in the presence of sodium nitroprusside (SNP) or sodium nitrite (SN), both of which liberate NO. Alone, neither SNP nor SN elicited neurite outgrowth from PC12 cells. However, like guanosine, both SNP and SN enhanced NGF-mediated neurite outgrowth in a synergistic manner as shown for the addition of SN in FIG. 21. Further confirming the effect, FIGS. 22A and 22B show that the neurotogenic properties of the NO donors were inhibited by both hemoglobin (Hb) and methemoglobin (MB). Both are substances which scavenge NO and CO with high affinity and preclude these agents from being used as signal transmitters.

Figure 23:
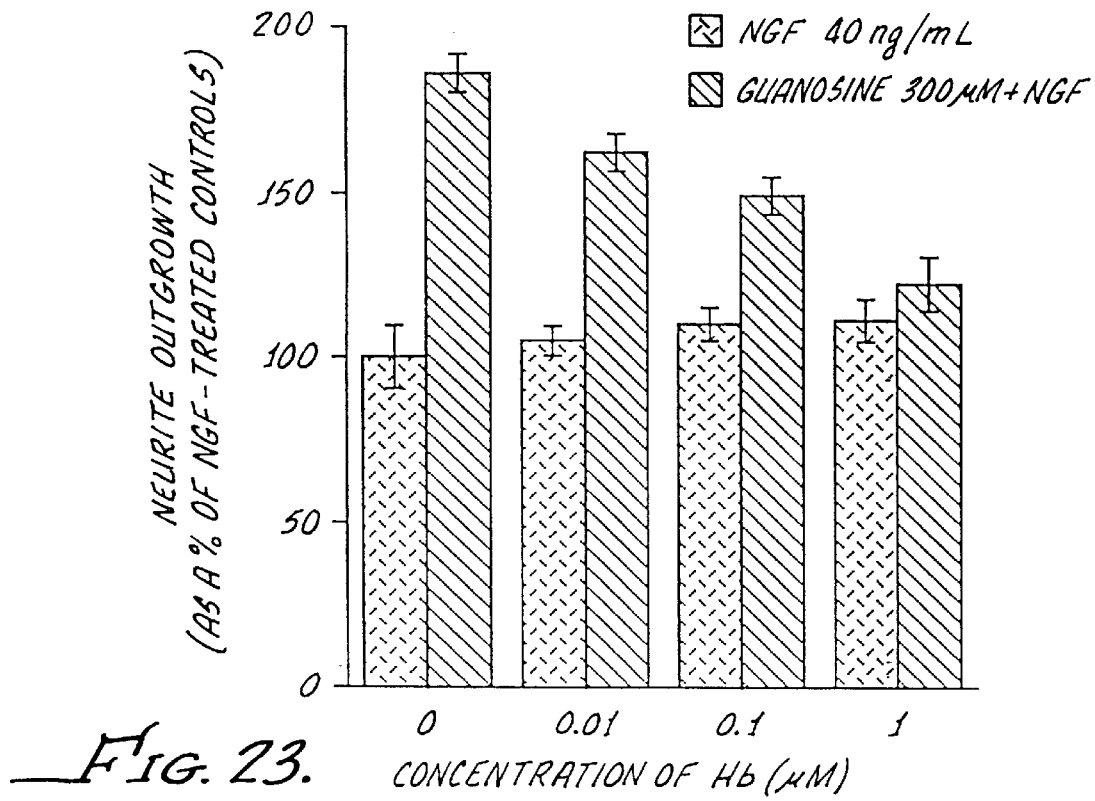
FIG. 23 is a graphical comparison showing the nerve growth factor mediated neurotogenic response of cells grown in various concentrations of hemoglobin with or without the purine derivative guanosine.

Accordingly, if NO or CO mediates the neurotogenic effects of guanosine, then these effects should be reduced by addition of hemoglobin to the cultures. The expected effect is clearly shown in FIG. 23 where Hb (0.1–1 mM) inhibited the neurotogenic effects of guanosine but not those of NGF. This indicates that the neurotogenic action of guanosine, but not that of NGF, requires synthesis of NO or CO.

Several facts indicate that it is CO rather than NO which interacts with guanosine to modify neural activity. For example, if the effects of guanosine were mediated through NO, then addition of guanosine to the PC12 cells should stimulate cNOS in PC12 cells to produce NO. However, cNOS had not been reported in PC12 cells and untreated (guanosine and NGF naive) PC12 cells did not stain for diaphorase, an enzyme that co-localizes with NOS. Since cNOS is calcium/calmodulin-sensitive, its activity should increase after adding a calcium ionophore, thus leading to increased cGMP levels. Addition of the ionophore A23187 to cultures of PC12 cells failed to elicit an increase in cGMP.

EXAMPLE 34

Carbon Monoxide, Not Nitric Oxide, Mediates the Effects of Guanosine on Neuritogenesis Based on the results of the previous examples, studies were performed to demonstrate that the purine derivatives of the present invention, including guanosine, modulate the carbon monoxide-dependent guanylyl cyclase system to modify neural activities.

Figure 24:
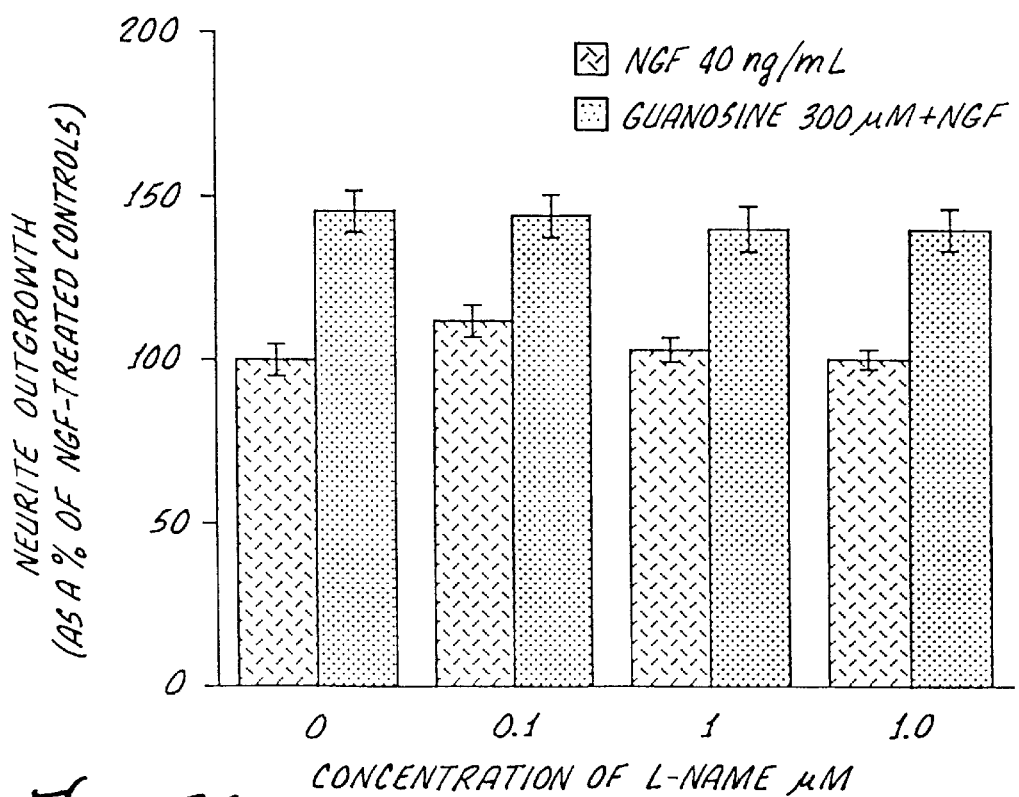
FIG. 24 is a graphical comparison showing the nerve growth factor mediated neurotogenic response of cells grown in various concentrations of L-nitro arginine methylester (L-NAME) with and without the purine derivative guanosine.

As in Example 6 where it was shown that carbon monoxide mediates the effects of AIT-082 through the use of inhibitors, the same techniques demonstrate that guanosine also interacts with the carbon monoxide dependent system. Specifically, as shown in FIG. 24, the cNOS inhibitor L-nitro arginine methyl ester (L-NAME) did not affect the ability of guanosine to enhance NGF-mediated neurite outgrowth. These data confirm that cNOS was not involved in the signal transduction pathway that mediated the neurotogenic effects of guanosine on PC12 cells.

Figure 25:
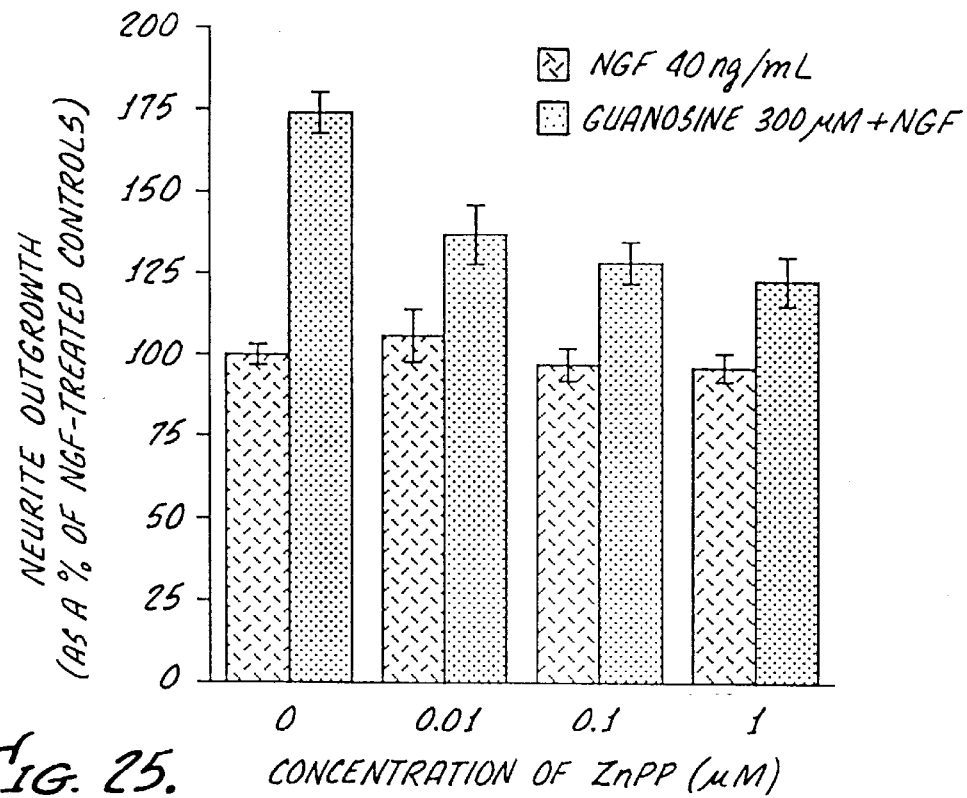
FIG. 25 is a graphical comparison of the nerve growth factor mediated neurotogenic response for cells grown in the presence of various concentrations of zinc protoporphyrin IX (ZNPP), an inhibitor of CO synthesis, with and without guanosine.
Figure 26:
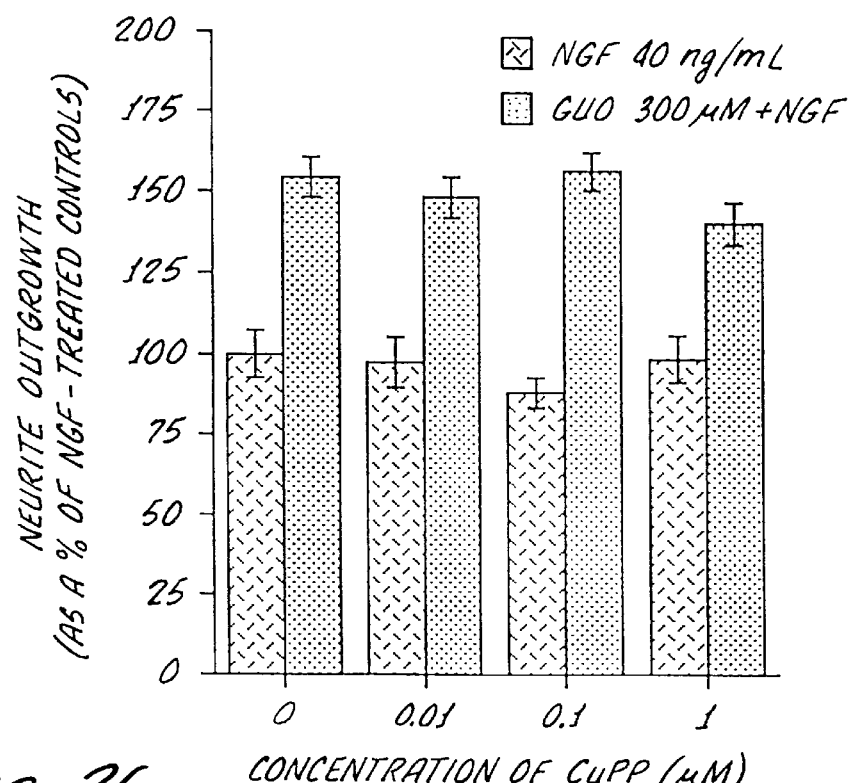
FIG. 26 is a negative control for the graphical comparison shown in FIG. 25 and is a graphical comparison of nerve growth factor mediated neurotogenic response for cells grown in various concentrations of copper protoporphyrin IX (CUPP), with and without the purine derivative guanosine.

To further demonstrate that CO, rather than NO, mediated the neurotogenic effects of guanosine, zinc protoporphyrin IX (ZnPP), which inhibits heme oxygenase and hence inhibits CO synthesis, was added to the cells during growth. As shown in FIG. 25, ZnPP abolished the neurotogenic effects of guanosine, but did not affect those of NGF. In contrast, a related protoporphyrin derivative, copper protoporphyrin IX (CuPP), does not inhibit heme oxygenase. Accordingly, FIG. 26 shows that copper protoporphyrin IX did not reduce the ability of guanosine to enhance NGF-dependent neurite outgrowth from PC12 cells. As with AIT-082, these data indicated that guanosine increased CO synthesis. In turn, CO activated sGC and increased intracellular GMP, thereby promoting neuritogenesis.

EXAMPLE 35

Inosine Pranobex Enhances Neuritogenesis

To provide further evidence of the scope and operability of the present invention, neurotogenic studies were performed using inosine pranobex. Specifically, inosine pranobex is a mixture of inosine and DIP-PacBa at a 1:3 molar ratio. Various concentrations of this compound were added to PC12 cells with NGF which were then monitored according to the protocol of Example 12.

Figure 27:
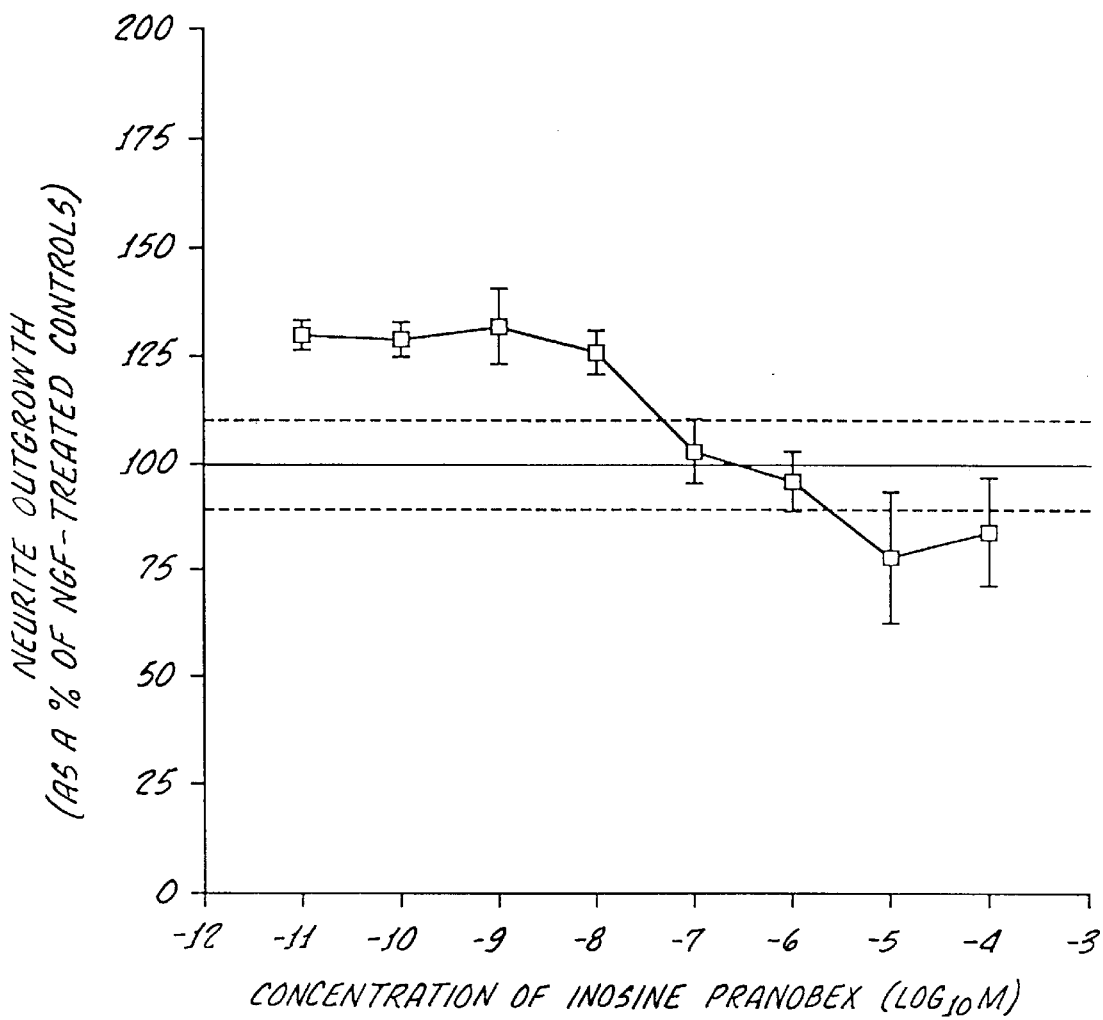
FIG. 27 is a graphical representation of the nerve growth factor mediated neurotogenic response for neuron cells grown in the presence of various concentrations of the purine derivative inosine pranobex.

As shown in FIG. 27, inosine pranobex substantially enhanced the amount of neurite outgrowth of the treated cells. The curve shown in FIG. 27 represents the different levels of inosine pranobex plus saturating concentrations of NGF while the horizontal lines represent the NGF control with attendant confidence levels. Here the treated cells are above the control baseline at most of the selected concentrations.

The modification of neural activity in accordance with the teachings of the present invention may be used to treat neurodegenerative diseases in order to provide recovery of neural function. Thus the methods of the present invention may be used to treat neurodegeneration from any cause including disease, trauma, age and exposure to harmful physical or chemical agents. Similarly, the methods disclosed herein may be used to treat neurological diseases including, but not limited to, Alzheimer's Disease and related degenerative disorders, Parkinson's disease and related disorders such as striato-nigral degeneration, spino-cerebellar atrophies, motor neuronopathies or "motor system diseases" including Amyotrophic Lateral Sclerosis, Werdnig-Hoffmann disease, Wohlfart-Kugelberg-Welander syndrome and hereditary spastic diplegia, damage to neurons by ischemia (as in strokes), anoxia, or hypoglycemia (as, for example after prolonged circulatory arrest), Huntington's disease, cerebral palsy, multiple sclerosis, psychiatric disorders including affective disorders, schizophrenia, epilepsy and seizures, peripheral neuropathies from any cause, learning disabilities and disorders of memory. Also, damage to neurons or their processes by physical agents such as radiation or electrical currents or by chemical agents including alcohol, aluminum, heavy metals, industrial toxins, natural toxins and legal or illegal drugs may be treated. The methods may further be used to treat victims of trauma to the brain or spinal cord resulting in neuronal damage or age related conditions such as benign forgetfulness and deterioration of sensory, motor, reflex or cognitive abilities due to loss of neurons or neuronal connectivity. Simply administering an effective dosage of the carbon monoxide dependent guanylyl cyclase modulating purine derivative to a subject suffering from any of the foregoing neural disorders will induce intracellular neuronal changes producing restoration of function.

Specifically, modification of the carbon monoxide dependent guanylyl cyclase system in accordance with the methods of the present invention produces changes in neural activity in neurons and glia cells including astrocytes. For example, using the present invention the neural activity of astrocytes may be modified to synthesize various neurotrophic factors and cytokines including fibroblast growth factor (FGF), nerve growth factor (NGF), brain derived neurotrophic factor (BDNF) and neurotrophin-3 (NT-3). These factors can influence the sprouting of neuritic processes from surviving neurons as well as promote the development of new cells. New synapses may then form and provide some recovery of function. These neurotrophic factors also play a neuroprotective role, thus inducing their production can ameliorate further neural damage.

Numerous purine derivatives may be used in accordance with the teachings of the present invention. However, the ability to modify neural activity by modulating the carbon monoxide dependent guanylyl cyclase system is not a general property of all purines or purine derivatives. For example, as shown in the data below, inosine, adenosine, hypoxanthine and xanthine were all relatively ineffective at modifying neural activity. Other purine derivatives which failed to modify neural activity include 3-(6-amino-9H-purin-9-yl)propionic acid, ethyl ester (AIT-0026), 3-(1,6-dihydro-6-oxo-9H-purin-9-yl)-N-{3-(2-oxopyrolidin-1-yl) propyl)propanamide (AIT-0034) and propentofylline. Moreover, while other purines and purine derivatives such as 5'-N-ethylcarboxamidoadenosine (NECA) were shown to stimulate neurite outgrowth, they did not do so by modulation of the carbon monoxide dependent guanylyl cyclase mechanism. Accordingly, the scope of the invention is defined by the functional reactivity of purine derivatives which modify neural activity as described herein and as shown by the data presented. Of course, those skilled in the art will appreciate that functionally equivalent isomers, analogs and homologs of the compounds of the present invention may be substituted to provide the desired neural modifications.

Those skilled in the art will further appreciate that the present invention may be embodied in other specific forms without departing from the spirit or central attributes thereof In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A method for selectively and controllably inducing the in vivo genetic expression of at least one naturally occurring genetically encoded molecule that stimulates neuritogenesis in a mammal, said method comprising the step of administering an effective amount of at least one carbon monoxide dependent guanylyl cyclase modulating purine derivative.

2. The method of claim 1 wherein said carbon monoxide dependent guanylyl cyclase modulating purine derivative is selected from the group consisting of guanosine, 4-((3-(1, 6-dihydro-6-oxo-9H-purin-9-yl)-1-oxopropyl)amino) benzoic acid, and inosine pranobex.

3. The method of claim 1 wherein said effective amount of said at least one carbon monoxide dependent guanylyl cyclase modulating purine derivative produces a treating concentration of at least 1 $\mu$M.

4. The method of claim 1 wherein said at least one carbon monoxide dependent guanylyl cyclase modulating purine derivative is orally administered to said mammal.

5. The method of claim 1 wherein said at least one carbon monoxide dependent guanylyl cyclase modulating purine derivative is administered to said mammal by injection.

6. A method for the effective direct administration of at least one naturally occurring genetically encoded molecule that stimulates neuritogenesis in a mammal, said method comprising the step of selectively inducing the in vivo genetic expression of said molecule that stimulates neuritogenesis in said mammal through the administration of an effective amount of at least one carbon monoxide dependent guanylyl cyclase modulating purine derivative to said mammal to effectively directly administer the at least one naturally occurring genetically encoded molecule that stimulates neuritogenesis.

7. The method of claim 6 wherein said carbon monoxide dependent guanylyl cyclase modulating purine derivative is selected from the group consisting of guanosine, 4-((3-(1, 6-dihydro-6-oxo-9H-purin-9-yl)-1-oxopropyl)amino) benzoic acid, and inosine pranobex.

8. The method of claim 6 wherein said effective amount of said at least one carbon monoxide dependent guanylyl cyclase modulating purine derivative produces a treating concentration of at least 1 $\mu$M.

9. The method of claim 6 wherein said at least one carbon monoxide dependent guanylyl cyclase modulating purine derivative is orally administered to said mammal.

10. The method of claim 6 wherein said at least one carbon monoxide dependent guanylyl cyclase modulating purine derivative is administered to said mammal by injection.

11. The method of claim 1 wherein the naturally occurring genetically encoded molecule that stimulates neuritogenesis is selected from the group consisting of neurotrophins and pleiotrophins.

12. The method of claim 11 wherein the neurotrophins and pleiotrophins are selected from the group consisting of NGF, FGF-2, and NT-3.

13. The method of claim 1 wherein the naturally occurring genetically encoded molecule that stimulates neuritogenesis is a naturally occurring genetically encoded molecule selected from the group consisting of NGF, FGF-2, NT-3, BDNF, CNTF, S100$\beta$, TGF$\beta_1$, and GDNF.

14. The method of claim 6 wherein at least one naturally occurring genetically encoded molecule that stimulates neuritogenesis is selected from the group consisting of neurotrophins and pleiotrophins.

15. The method of claim 14 wherein the neurotrophins and pleiotrophins are selected from the group consisting of NGF, FGF-2, and NT-3.

16. The method of claim 6 wherein the naturally occurring genetically encoded molecule that stimulates neuritogenesis is a naturally occurring genetically encoded molecule selected from the group consisting of NGF, FGF-2, NT-3, BDNF, CNTF, S100$\beta$, TGFP$\beta_1$, and GDNF.

* * * * *

UNITED STATES PATENT AND TRADEMARK OFFICE
CERTIFICATE OF CORRECTION

PATENT NO. : 6,027,936
DATED : February 22, 2000
INVENTOR(S) : Glasky

It is certified that error appears in the above-identified patent and that said Letters Patent is hereby corrected as shown below:

On Title page, below United States Patent [19], the inventor should be "Glasky et al."

On Title page, at item [76] Inventor, it should read:
"Alvin J. Glasky, 12231 Pevero, Tustin, Calif. 92680; Michael P. Rathbone, 40 Spadina Avenue, Hamilton, Ontario, Canada L8M 2X1"

Signed and Sealed this

Nineteenth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,027,936
DATED : February 22, 2000
INVENTOR(S) : Glasky

It is certified that error appears in the above-identified patent and that said Letters Patent is hereby corrected as shown below:

<u>Title page,</u>
Item [19], the inventor should be "Glasky et al."
Item [76], Inventor, it should read: "Alvin J. Glasky, 12231 Pevero, Tustin, Calif. 92680;
Michel P. Rathbone, 40 Spadina Avenue, Hamilton, Ontario, Canada L8M 2X1"

Signed and Sealed this

Ninth Day of October, 2001

Attest:

NICHOLAS P. GODICI
Attesting Officer
Acting Director of the United States Patent and Trademark Office